(12) United States Patent
Inoue et al.

(10) Patent No.: US 7,939,821 B2
(45) Date of Patent: *May 10, 2011

(54) ORGANOMETALLIC COMPLEX, AND LIGHT EMITTING ELEMENT AND ELECTRONIC APPLIANCE USING THE SAME

(75) Inventors: Hideko Inoue, Kanagawa (JP); Satoshi Seo, Kanagawa (JP)

(73) Assignee: Semiconductor Energy laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/691,003

(22) Filed: Jan. 21, 2010

(65) Prior Publication Data

US 2010/0117068 A1 May 13, 2010

Related U.S. Application Data

(63) Continuation of application No. 11/499,569, filed on Aug. 4, 2006, now Pat. No. 7,652,283.

(30) Foreign Application Priority Data

Aug. 9, 2005 (JP) .................................. 2005-230660

(51) Int. Cl.
*H01L 51/54* (2006.01)
*C07F 15/00* (2006.01)

(52) U.S. Cl. .................. 257/40; 257/103; 257/E51.044; 313/504; 544/225; 428/690

(58) Field of Classification Search ............. 257/40, 257/103, E51.001–E51.052; 313/504; 428/690; 438/99; 544/225, 229
See application file for complete search history.

(56) References Cited

U.S. PATENT DOCUMENTS 6,303,238 B1   10/2001   Thompson et al.
(Continued)

FOREIGN PATENT DOCUMENTS

JP    2005-239648    9/2005
(Continued)

OTHER PUBLICATIONS

Tsutsui, T. et al, "The Operation Mechanism and the Light Emission Efficiency of the Organic EL Element," Textbook for the 3$^{rd}$ Workshop, Division of Molecular Electronics and Bioelectronics, Japan Society of Applied Physics, 1993, pp. 31-37; w/English translation (11 pages).

(Continued)

*Primary Examiner* — Matthew W Such
(74) *Attorney, Agent, or Firm* — Husch Blackwell LLP

(57) ABSTRACT

It is an object of the present invention to provide a substance which can emit red phosphorescence which is closer to the chromaticity coordinates of red according to the NTSC standard. The present invention provides an organometallic complex represented by the general formula (1), wherein each of R1 to R3 represents any one of hydrogen, a halogen group, an acyl group, an alkyl group, an alkoxyl group, an aryl group, a cyano group, and a heterocyclic group, and at least one of $R^1$ to $R^3$ represents an electron-withdrawing group; and M represents a Group 9 element or a Group 10 element, and when M is the Group 9 element, n=2, whereas when M is the Group 10 element, n=1. Such an organometallic complex can emit red phosphorescence with good spectral luminous efficiency which is closer to the chromaticity coordinates of red according to the NTSC standard.

(1)

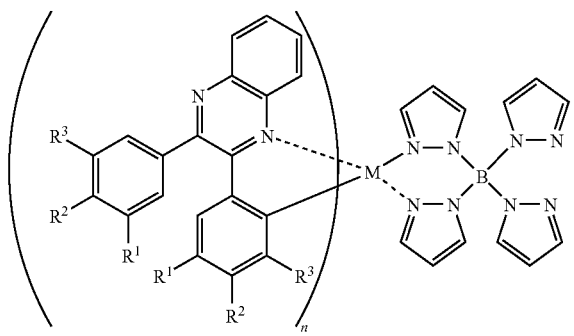

36 Claims, 11 Drawing Sheets

U.S. PATENT DOCUMENTS

| | | | |
|---|---|---|---|
| 7,482,451 B2 | 1/2009 | Thompson et al. | |
| 7,652,283 B2 * | 1/2010 | Inoue et al. | 257/40 |
| 2001/0045565 A1 | 11/2001 | Yamazaki | |
| 2002/0034659 A1 | 3/2002 | Nishi et al. | |
| 2004/0102632 A1 | 5/2004 | Thompson et al. | |
| 2004/0230061 A1 | 11/2004 | Seo et al. | |
| 2005/0003232 A1 | 1/2005 | Shitagaki et al. | |
| 2005/0065342 A1 | 3/2005 | Shitagaki et al. | |
| 2005/0191527 A1 | 9/2005 | Fujii et al. | |
| 2005/0233170 A1 | 10/2005 | Yamazaki | |
| 2005/0242715 A1 | 11/2005 | Inoue et al. | |
| 2006/0078758 A1 | 4/2006 | Lin | |
| 2006/0240278 A1 * | 10/2006 | Hatwar et al. | 428/690 |
| 2007/0037010 A1 * | 2/2007 | Vestweber et al. | 428/690 |
| 2009/0033209 A1 | 2/2009 | Seo et al. | |

FOREIGN PATENT DOCUMENTS

| | | |
|---|---|---|
| WO | WO 00/70655 A2 | 11/2000 |
| WO | WO 01/41512 A1 | 6/2001 |
| WO | WO 2005034260 A1 * | 4/2005 |
| WO | WO 2005/115061 A1 | 12/2005 |
| WO | WO 2006/059802 A1 | 6/2006 |
| WO | WO 2006/104177 A1 | 10/2006 |

OTHER PUBLICATIONS

Duan, J.-P. et al, "New Iridium Complexes as Highly Efficient Orange-Red Emitters in Organic Light-Emitting Diodes," Advanced Materials, vol. 15, No. 3, Feb. 5, 2003, pp. 224-228.

Li, J. et al, "Synthesis and Characterization of Cyclometalated Ir(III) Complexes with Pyrazolyl Ancillary Ligands," Polyhedron, vol. 23, 2004, pp. 419-428.

Fujii, H. et al, "Highly Efficient and Vivid-Red Phosphors Bearing 2,3-Diphenylquinoxaline Units and Their Application to Organic Light-Emitting Devices," IEICE Trans. Electron, vol. E87-C, No. 12, Dec. 2004, pp. 2119-2121.

Office Action re Chinese application No. CN 200610114845.9, dated Jun. 13, 2010 (with English translation).

* cited by examiner

ORGANOMETALLIC COMPLEX, AND LIGHT EMITTING ELEMENT AND ELECTRONIC APPLIANCE USING THE SAME

This application is a continuation of application Ser. No. 11/499,569 filed on Aug. 4, 2006 now U.S. Pat. No. 7,652,283.

BACKGROUND OF THE INVENTION

1. Field of the Invention

The present invention relates to an organometallic complex which can convert an excited triplet state into light emission, a light emitting element using the organometallic complex, and a light emitting device using the light emitting element.

2. Description of the Related Art

A light emitting element using an organic compound is an element in which a layer containing an organic compound or an organic compound film emits light by applying an electrical field. A light emission mechanism of a light emitting element is as follows: electrons injected from a cathode and holes injected from an anode are recombined in the organic compound film to form a molecular exciton by applying a voltage to a pair of electrodes with the organic compound film interposed therebetween, and then energy is released to emit light when the molecular exciton returns to a ground state.

In such a light emitting element, generally, an organic compound film is formed by a thin film of less than 1 μm. In addition, since such a light emitting element is a self-light emitting element in which the organic compound film itself emits light, a backlight used for a conventional liquid crystal display is not required. Therefore, such a light emitting element has a great advantage of being able to be manufactured to be significantly thin and lightweight. In addition, for example, in a light emitting element having an organic compound film with a thickness of approximately 100 to 200 nm, the time from injection of carriers to recombination is approximately several tens of nanoseconds in consideration of the carrier mobility of the organic compound film, and the time required for light-emission is about microseconds or less, even when including a process from the recombination of carriers to the emission of light. Therefore, it is also one of features that the response speed is quite fast. Further, since such a light emitting element is a carrier-injection type light emitting element, driving at DC voltage is possible and noise is not easily generated.

In addition to element characteristics such as thinness, lightweight, high-speed response, and direct-current low-voltage driving as described above, it can be also said to be one of great advantages that a color of light emission from a light emitting element using an organic compound is rich in variation. It is because of the variety of organic compounds themselves. That is, richness of colors is produced by flexibility of the organic compound in which materials having various colors of light emission can be developed by molecular design (for example, introduction of a substituent) or the like. It can be said that the biggest application field of a light emitting element utilizing this richness of colors is a full-color flat-panel display.

It can be said that the above-described element characteristics such as thinness, lightweight, high-speed response, and DC low-voltage driving are also appropriate characteristics for a flat-panel display. In recent years, the use of phosphorescent materials instead of fluorescent materials has been tried as an attempt at further improvement in light emitting efficiency. In a light emitting element using an organic compound, light emission from an excited singlet state (S*) (fluorescence) and light emission from an excited triplet state (T*) (phosphorescence) can be exhibited. When a fluorescent material is used, only light emission (fluorescence) from S* contributes.

However, it is considered that a statistical generation ratio of S* to T* of a light emitting element is S*:T*=1:3 (for example, see Non-Patent Document 1). Accordingly, in the case of a light emitting element using a fluorescent material, the theoretical limit of an internal quantum efficiency (the ratio of generated photons to injected carriers) is considered to be 25% on the ground of S*:T*=1:3. In other words, in the case of a light emitting element using a fluorescent material, at least 75% of injected carriers are wasted uselessly.

Conversely, it is believed that luminous efficiency is improved (simply, by 3 to 4 times) if light emission from T*, that is, phosphorescence can be used. However, in the case of a commonly used organic compound, light emission from T* (phosphorescence) is not observed at room temperature, and normally, only light emission from S* (fluorescence) is observed. In recent years, however, light emitting elements in which energy that is emitted while returning from T* to a ground state (hereinafter, referred to as triplet excitation energy) can be converted into light emission have been released one after another, and the high light emission efficiency thereof has attracted attentions (for example, see Non-Patent Document 2).

In Non-Patent Document 2, an iridium complex using a dibenzo[f, h]quinoxaline derivative for a ligand is synthesized and used as a light emitting substance of a light emitting element. The obtained light emitting element has high luminous efficiency; however, the color of light emission therefrom is orange-red, and red light emission with high color purity is not realized.

On the other hand, in Non-Patent Document 3, deep-red light emission with CIE chromaticity coordinates of (x, y)= (0.70, 0.28) is achieved with an iridium complex having 2,3-diphenylquinoxaline as a ligand.

Non-Patent Document 1

Tetsuo TSUTSUI, Textbook for the 3rd Workshop, Division of Molecular Electronics and Bioelectronics, Japan Society of Applied Physics, p. 31 (1993).

Non-Patent Document 2

J. Duan et al., Advanced Materials, (2003), 15, No. 3, February 5, pp. 224-228

Non-Patent Document 3

Hiroyuki FUJII et al., IECE TRANS. ELECTRON., vol. E87-C, No. 12, December (2004), pp. 2119-2121

However, chromaticity coordinates of red are (x, y)=(0.67, 0.32), according to the NTSC (National Television System Committee) standard which is a standard for a full-color display. Therefore, when the iridium complex disclosed in Non-Patent Document 3 is used in a display device, chromaticity coordinates in a sending side from which image information is sent and those in a receiving side are not identical, accordingly, color reproducibility is not favorable. In addition, a wavelength obtained from a light emitting element is 675 nm, which means that spectral luminous efficiency is low compared with standard red; therefore, high luminance can not be obtained.

SUMMARY OF THE INVENTION

It is an object of the present invention to provide a substance which can emit red light emission with good spectral luminous efficiency which is closer to the chromaticity coordinates of red according to the NTSC standard, (x, y)=(0.67, 0.32).

After repeated earnest study, the inventors of the present invention have found that an organometallic complex represented by any one of the following general formulae (1) to (3) can emit red phosphorescence with good chromaticity which is closer to the red chromaticity coordinates according to the NTSC standard.

One of the organometallic complexes of the present invention is represented by the general formula (1).

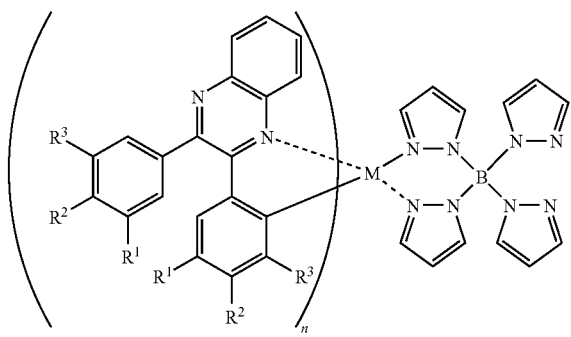

(1)

In the general formula (1), each of R1 to R3 represents any one of hydrogen, a halogen group, an acyl group, an alkyl group, an alkoxyl group, an aryl group, a cyano group, and a heterocyclic group, and at least one of $R^1$ to $R^3$ represents an electron-withdrawing group; and M represents a Group 9 element or a Group 10 element, and when M is the Group 9 element, n=2, whereas when M is the Group 10 element, n=1.

One of the organometallic complexes of the present invention is represented by the general formula (2).

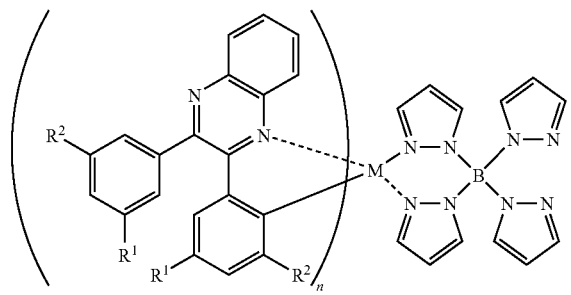

(2)

In the general formula (2), each $R^1$ and $R^2$ represents an electron-withdrawing group; and M represents a Group 9 element or a Group 10 element, and when M is the Group 9 element, n=2, whereas when M is the Group 10 element, n=1.

One of the organometallic complexes of the present invention is represented by the general formula (3).

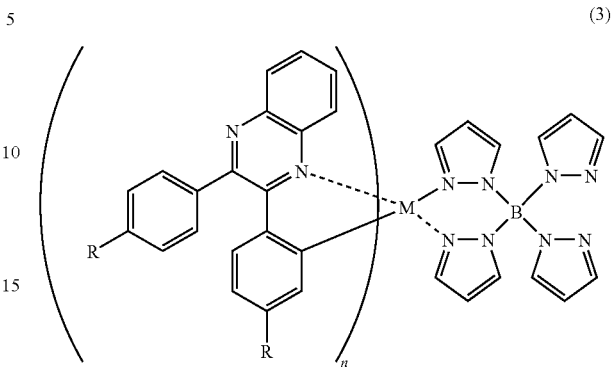

(3)

In the general formula (3), R represents an electron-withdrawing group; and M represents a Group 9 element or a Group 10 element, and when M is the Group 9 element, n=2, whereas when M is the Group 10 element, n=1.

In each of the organometallic complexes represented by the general formulae (1) to (3), the electron-withdrawing group is any one of a halogen group, a haloalkyl group, or a cyano group. Among halogen groups, a fluoro group which has a high electron withdrawing property is particularly preferable. Among haloalkyl groups, a trifluoromethyl group is particularly preferable.

In each of the organometallic complexes represented by the general formulae (1) to (3), central metal M is preferably a heavy metal, more preferably, iridium or platinum. Thus, a heavy atom effect can be obtained, thereby intersystem crossing is promoted and phosphorescence can be exhibited more efficiently.

One of the organometallic complexes of the present invention is represented by the general formula (2), wherein the electron-withdrawing group is a fluoro group, central metal M is iridium, and n=2.

One of the organometallic complexes of the present invention is represented by the general formula (3), wherein the electron-withdrawing group is a fluoro group, central metal M is iridium, and n=2.

One of the light emitting elements of the present invention has the organometallic complex represented by any one of the general formulae (1) to (3) between a pair of electrodes.

One of the light emitting elements of the present invention has the organometallic complex represented by any one of the general formulae (1) to (3) as a light emitting substance.

One of the light emitting devices of the present invention has a light emitting element including the organometallic complex represented by any one of the general formulae (1) to (3).

The organometallic complex or the light emitting element of the present invention can emit red phosphorescence with good spectral luminous efficiency which is closer to the red chromaticity coordinates according to the NTSC standard. In addition, since the light emitting element of the present invention can emit phosphorescence, the light emitting element of the present invention has high light emission efficiency.

The light emitting device of the present invention has good spectral luminous efficiency since it has an organometallic complex of the present invention as a light emitting substance. In addition, since the light emitting device can emit red phosphorescence which is closer to the red chromaticity coordinates according to the NTSC standard, red chromaticity coordinates in a sending side from which a signal conforming to the NTSC standard is transmitted to a driver circuit and those in a receiving side which exhibits light emission are almost identical. Therefore, a light emitting device with accurate color reproducibility with respect to inputted image information can be obtained.

DETAILED DESCRIPTION OF THE INVENTION

Figure 1:
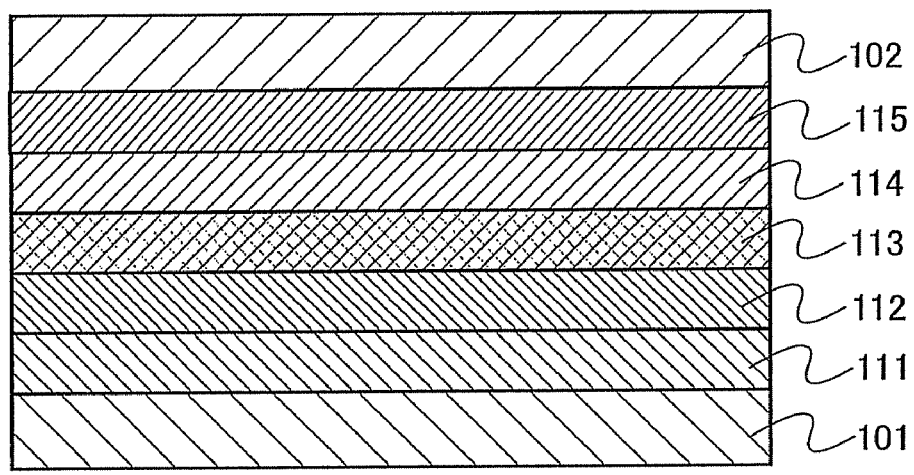
FIG. 1 is an element structure of a light emitting element of the present invention.

Hereinafter, embodiment modes of the present invention are explained with reference to the drawings. However, the present invention is not limited to the following description. As is easily understood to a person skilled in the art, the mode and the detail of the present invention can be variously changed without departing from the spirit and the scope of the present invention. Thus, the present invention is not interpreted as being limited to the following description of the embodiment modes.

Embodiment Mode 1

As examples of the present invention, organometallic complexes represented by the structural formulae (4) to (19) can be given. Note that the present invention is not limited to those described hereinafter.

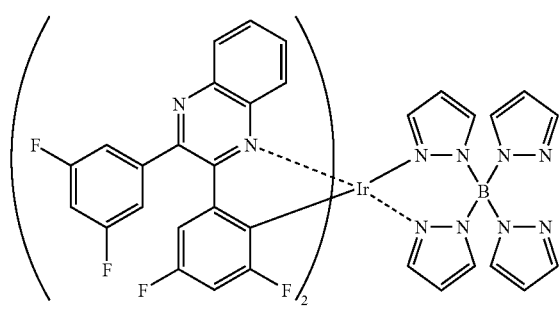
(4)

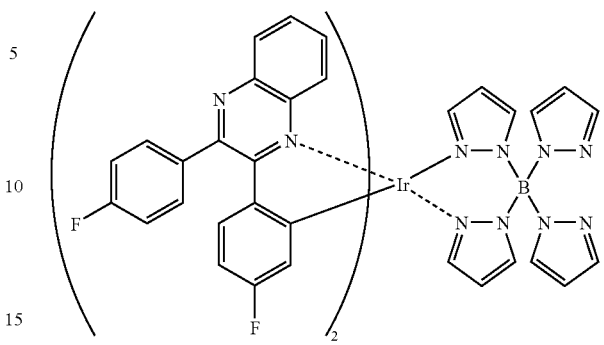
(5)

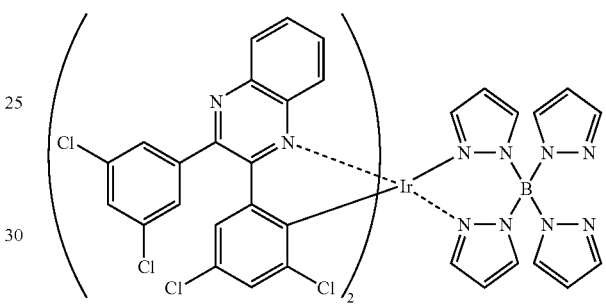
(6)

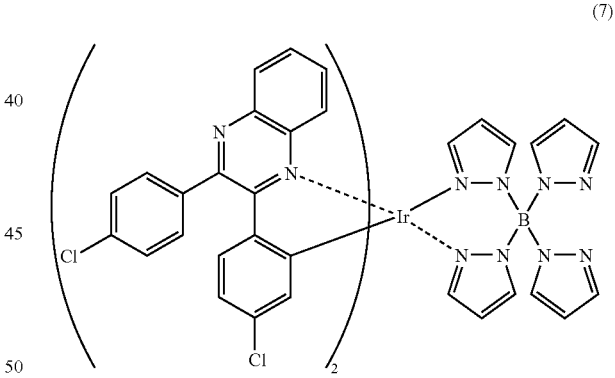
(7)

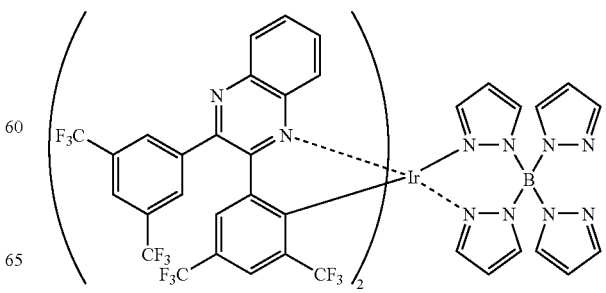
(8)

(9)
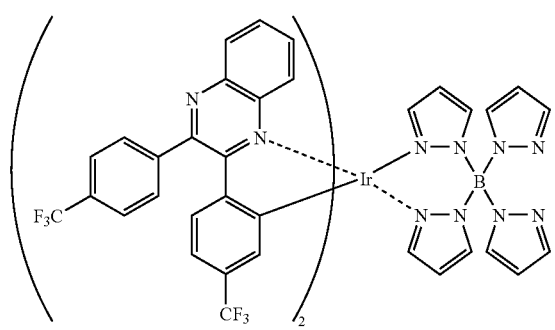
(13)
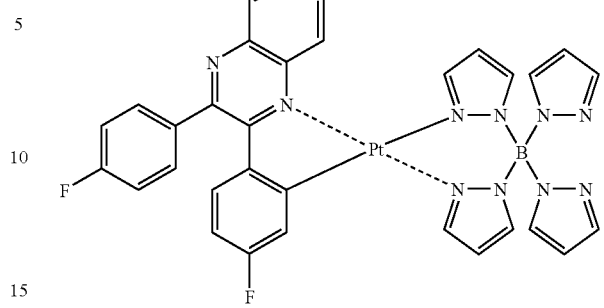
(10)
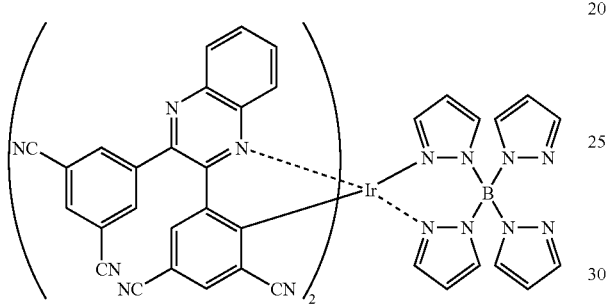
(14)
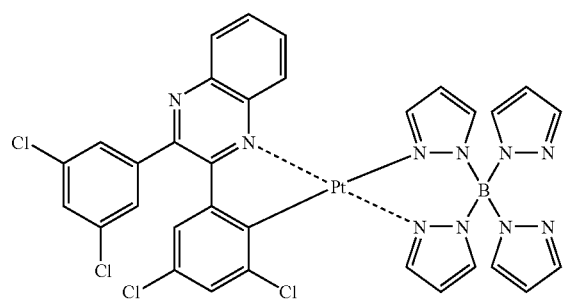
(11)
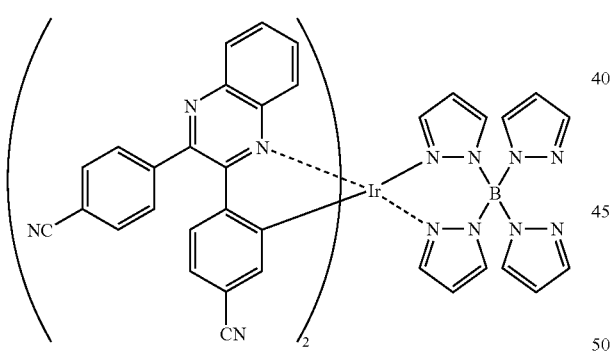
(15)
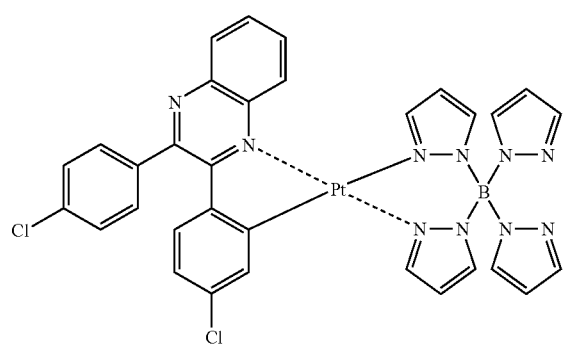
(12)
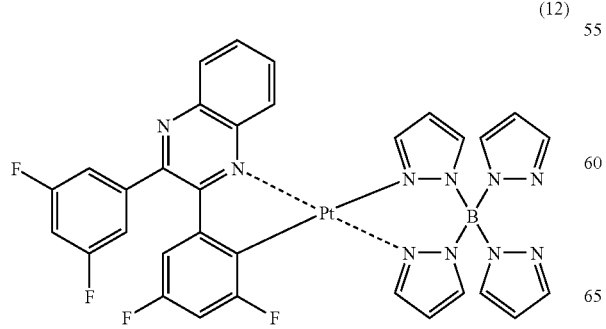
(16)
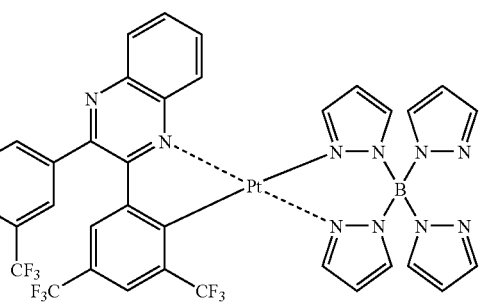

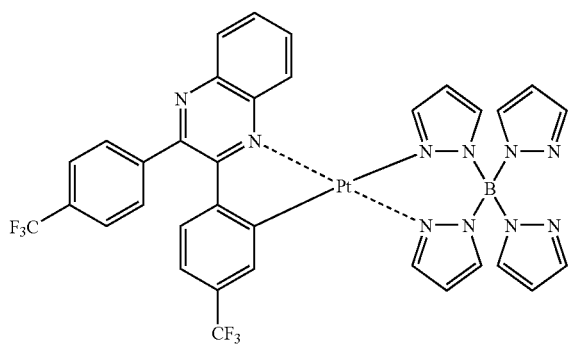

(17)

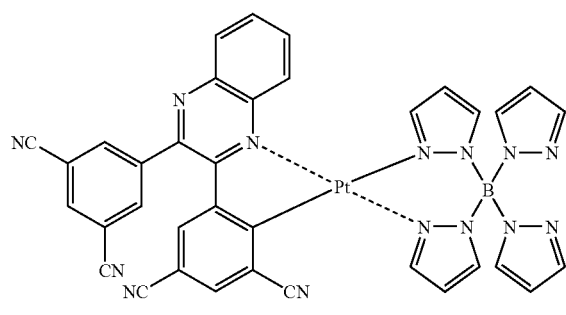

(18)

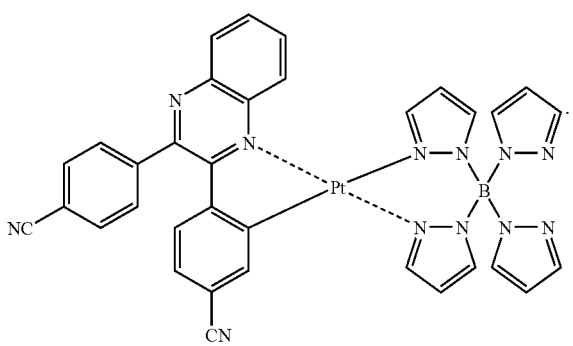

(19)

The foregoing organometallic complexes of the present invention can emit red phosphorescence with good spectral luminous efficiency which is closer to the red chromaticity coordinates according to the NTSC standard.

Embodiment Mode 2

The organometallic complex of the present invention can be obtained by an ortho-metalation reaction in which a compound represented by the following general formula (20) is arranged with a metal atom. A synthetic method of the organometallic complex represented by the foregoing general formula (1) using a ligand represented by the general formula (20) is described as follows.

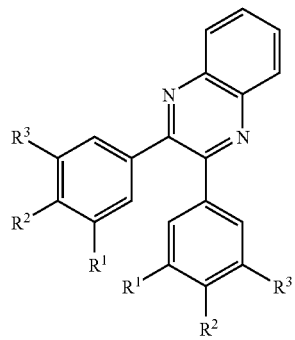

(20)

In the general formula (20), each of R1 to R3 represents any one of hydrogen, a halogen group, an acyl group, an alkyl group, an alkoxyl group, an aryl group, a cyano group, and a heterocyclic group. Note that at least one of $R^1$ to $R^3$ represents an electron-withdrawing group.

A ligand (a compound A) represented by the general formula (20) is synthesized by, for example, a reaction of a compound including benzyl in its skeleton with a compound including diamine in its skeleton according to the synthesis scheme (a-1).

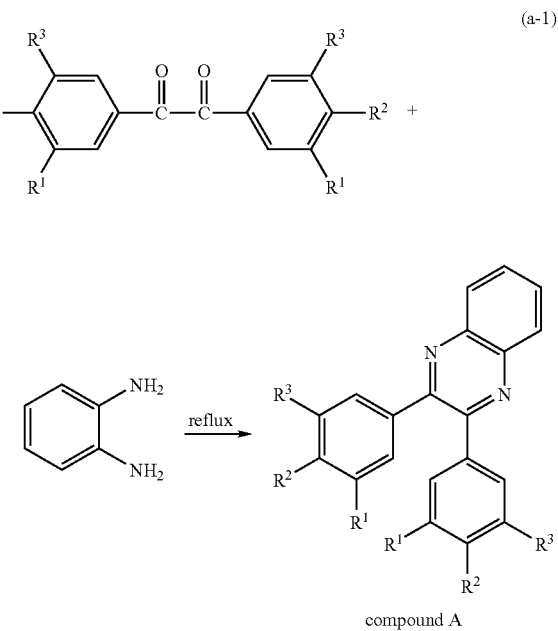

(a-1)

An organometallic complex which is used in the present invention is synthesized using thus the obtained ligand represented by the general formula (20).

For example, in the case of synthesizing an organometallic complex of the present invention using iridium as a central metal, the compound A is reacted with hydrate of iridium chloride that is a raw material of a central metal according to the synthesis scheme (a-2) to synthesize a compound B having a structure in which the compound A is arranged with iridium. The chlorine-bridged compound B is also referred to as a binuclear complex. The reaction according to the synthesis scheme (a-2) is referred to as an ortho-metalation reaction.

(a-2)

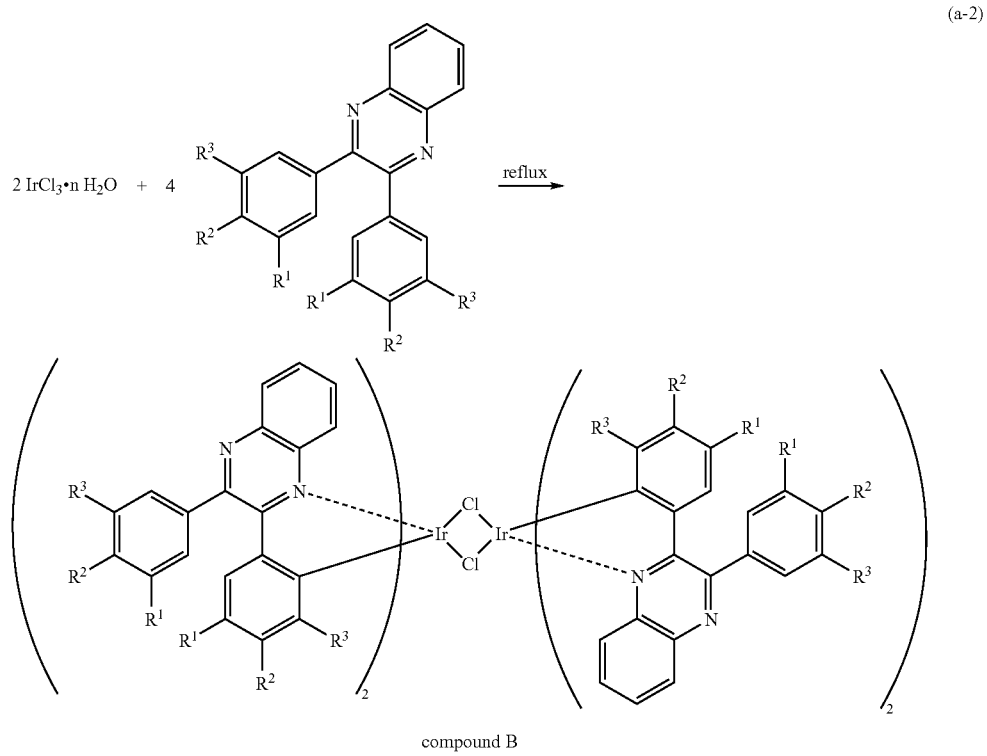

compound B

Then, the obtained binuclear complex which is the compound B and antichlor such as silver trifluoromethanesulfonate react as represented by the synthesis scheme (a-3) to precipitate silver chloride. Then, a supernatant solution thereof and potassium tetrapyrazolyl boronato (abbreviated as Kbpz$_4$) react. Thus, an organometallic complex represented by the general formula (21) of the present invention can be obtained.

(a-3)

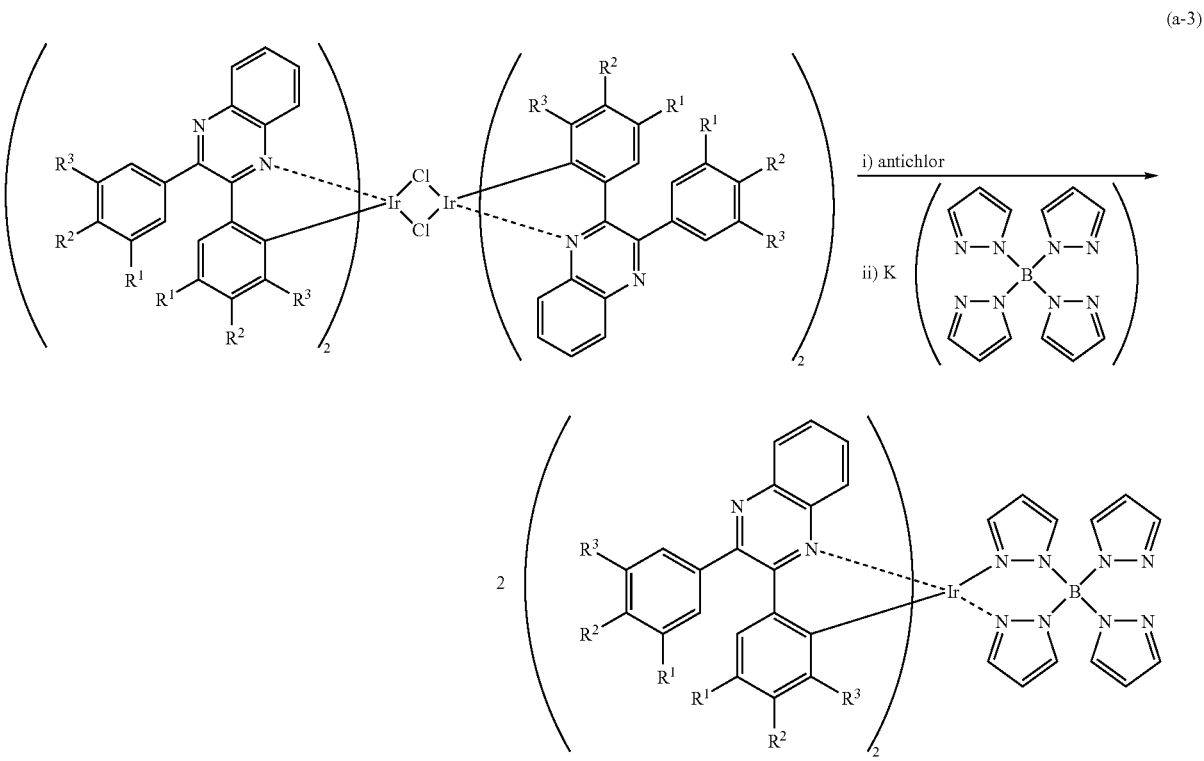

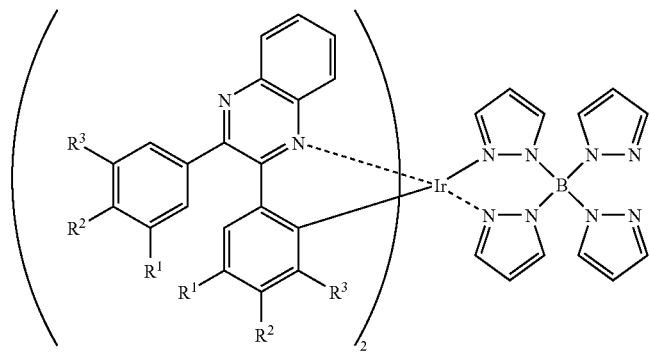

(21)

In the synthesis schemes (a-1), (a-2), and (a-3), and the general formula (21), each of R1 to R3 represents any one of hydrogen, a halogen group, an acyl group, an alkyl group, an alkoxyl group, an aryl group, a cyano group, and a heterocyclic group. Note that at least one of $R^1$ to $R^3$ represents an electron-withdrawing group. The electron-withdrawing group is preferably a halogen group, a haloalkyl group, or a cyano group.

Besides, an organometallic complex including platinum as a central metal can be obtained by replacing hydrate of iridium chloride by salt including platinum such as potassium tetrachloroplatinate.

The thus synthesized organometallic complex of the present invention can emit red phosphorescence with good spectral luminous efficiency which is closer to the red chromaticity coordinates according to the NTSC standard.

Embodiment Mode 3

A mode of a light emitting element using an organometallic complex of the present invention as a light emitting substance is explained with reference to FIG. 1.

FIG. 1 shows a light emitting element having a light emitting layer 113 between a first electrode 101 and a second electrode 102. The light emitting layer 113 contains the organometallic complex of the present invention represented by any one of the general formulae (1) to (3).

In addition to the light emitting layer 113, a hole injecting layer 111, a hole transporting layer 112, an electron transporting layer 114, an electron injecting layer 115, and the like are provided between the first electrode 101 and the second electrode 102. These layers are stacked so that holes are injected from the first electrode 101 side and electrons are injected from the second electrode 102 side when applying voltage so that potential of the first electrode 101 is higher than that of the second electrode 102.

In such a light emitting element, holes injected from the first electrode 101 side and electrons injected from the second electrode 102 side are recombined with each other in the light emitting layer 113 to excite the organometallic complex of the present invention in the light emitting layer. Then, the organometallic complex in the excited state emits light while returning to a ground state. Thus, the organometallic complex of the present invention serves as a light emitting substance.

The light emitting layer 113 may be a layer formed of only the organometallic complex of the present invention. Alternatively, the light emitting layer 113 is preferably formed by dispersing a light emitting substance into a layer formed of a substance (host) having a larger energy gap than that of the light emitting substance, in the case where concentration quenching occurs. Concentration quenching can be prevented by dispersing the organometallic complex of the present invention to be included in the light emitting layer 113. Note that an energy gap refers to an energy difference between an LUMO (Lowest Unoccupied Molecular Orbital) level and a HOMO (Highest Occupied Molecular Orbital) level.

A substance used to disperse the organometallic complex of the present invention is not particularly limited. In addition to a compound having an aryl amine skeleton such as 2,3-bis (4-diphenylaminophenyl)quinoxaline (abbreviated as TPAQn) or 4,4☐bis[N-(1-naphthyl)-N-phenylamino]biphenyl (abbreviated as NPB), a carbazole derivative such as 4,4☐bis(N-carbazolyl)biphenyl (abbreviated as CBP) or 4,4☐☐tris(N-carbazol)triphenylamine (abbreviated as TCTA), a metal complex such as bis[2-(2-hydroxyphenyl) pyridinato]zinc (abbreviated as $Znpp_2$), bis[2-(2-hydroxyphenyl)benzoxazolato]zinc (abbreviated as ZnBOX), or tris (8-quinolinolato)aluminum (abbreviated as $Alq_3$) is preferably used. One or two or more of these substances are selected to be mixed so that the organometallic complex of the present invention is dispersed. In particular, by mixing the organometallic complex of the present invention with a bipolar substance such as TPAQn which is described later, the organometallic complex of the present invention can emit light more efficiently. Such a layer containing mixed plurality of compounds can be formed by co-evaporation. Here, co-evaporation refers to an evaporation method in which raw materials are vaporized from respective evaporation sources provided in one processing chamber and the vaporized raw materials are mixed in a gas phase so as to be deposited over a subject.

Although an anode material for forming the first electrode 101 is not particularly limited, metal having a high work function (work function of 4.0 eV or higher), alloy, a conductive compound, or a mixture thereof are preferably used. As a specific example of such an anode material, in addition to indium tin oxide (abbreviated as ITO), ITO containing silicon oxide, or indium zinc oxide (abbreviated as IZO) formed using a target of indium oxide mixed with 2 to 20 wt % of zinc oxide (ZnO); Gold (Au), platinum (Pt), nickel (Ni), tungsten (W), chromium (Cr), molybdenum (Mo), iron (Fe), cobalt (Co), copper (Cu), palladium (Pd), or nitride of a metal material (such as TiN) can be given.

On the other hand, as a substance for forming the second electrode 102, metal having a low work function (work function of 3.8 eV or lower), alloy, a conductive compound, or a mixture thereof is preferably used. As a specific example of such a cathode material, an element which belongs to Group 1 or 2 of the Periodic Table, that is, an alkali metal such as lithium (Li) or cesium (Cs), an alkaline earth metal such as magnesium (Mg), calcium (Ca), or strontium (Sr), or an alloy thereof (Mg:Ag, Al:Li) can be given. However, by providing an electron generating layer described later between the second electrode 102 and the light emitting layer 113 so as to be stacked with the second electrode, various conductive materials including the material which has been given as the material for the first electrode 101 such as Al, Ag, ITO, or ITO containing silicon oxide can be used for the second electrode 102 regardless of the magnitude of the work function.

The first electrode 101 and the second electrode 102 are formed of the foregoing anode materials and cathode materials, respectively, by an evaporation method, a sputtering method, or the like to have a thickness of preferably 10 to 500 nm.

In addition, as shown in FIG. 1, the hole transporting layer 112 may be formed between the first electrode 101 and the light emitting layer 113. Here, the hole transporting layer is a layer having a function of transporting holes injected from the first electrode 101 side to the light emitting layer 113. By forming the hole transporting layer 112, the distance between the first electrode 101 and the light emitting layer 113 can be increased. As a result, quenching due to metal contained in the first electrode 101 can be prevented. The hole transporting layer is preferably formed of a substance having a high hole transporting property, particularly, a substance having a hole mobility of $1 \times 10^{-6}$ cm$^2$/Vs or higher. Note that a substance having a high hole transporting property refers to a substance having higher mobility of holes than that of electrons. As a specific example of a substance which can be used for forming the hole transporting layer 112, 4,4'-bis[N-(1-naphthyl)-N-phenylamino]biphenyl (abbreviated as NPB), 4,4'-bis[N-(3-methylphenyl)-N-phenylamino]biphenyl (abbreviated as TPD), 4,4',4''-tris(N,N-diphenylamino)triphenylamine (abbreviated as TDATA), 4,4',4''-tris[N-(3-methylphenyl)-N-phenylamino]triphenylamine (abbreviated as MTDATA), 4,4'-bis{N-[4-(N,N-di-m-tolylamino)phenyl]-N-phenylamino}biphenyl (abbreviated as DNTPD), 1,3,5-tris[N,N-di(m-tolyl)amino]benzene (abbreviated as m-MTDAB), 4,4',4''-tris(N-carbazolyl)triphenylamine (abbreviated as TCTA), phthalocyanine (abbreviated as H$_2$Pc), copper phthalocyanine (abbreviated as CuPc), vanadylphthalocyanine (abbreviated as VOPc), or the like can be given. In addition, the hole transporting layer 112 can be formed to have a multilayer structure formed by combining two or more of layers made of the foregoing substances.

As shown in FIG. 1, the electron transporting layer 114 may be formed between the second electrode 102 and the light emitting layer 113. Here, an electron transporting layer is a layer having a function of transporting electrons injected from the second electrode 102 to the light emitting layer 113. By providing the electron transporting layer 114, the distance between the second electrode 102 and the light emitting layer 113 can be increased. As a result, quenching due to metal contained in the second electrode 102 can be prevented. The electron transporting layer is preferably formed of a substance having a high electron transporting property, particularly, a substance having an electron mobility of $1 \times 10^{-6}$ cm$^2$/Vs or higher. Note that a substance having a high electron transporting property refers to a substance having higher mobility of electrons than that of holes. As a specific example of a substance which can be used for forming the electron transporting layer 114, in addition to a metal complex such as tris(8-quinolinolato)aluminum (abbreviated as Alq$_3$), tris(4-methyl-8-quinolinolato)aluminum (abbreviated as Almq$_3$), bis(10-hydroxybenzo[h]-quinolinato)beryllium (abbreviated as BeBq$_2$), bis(2-methyl-8-quinolinolato)-4-phenylphenolato-aluminum (abbreviated as BAlq), bis[2-(2-hydroxyphenyl)benzoxazolato]zinc (abbreviated as Zn(BOX)$_2$), and bis[2-(2-hydroxyphenyl)benzothiazolato]zinc (abbreviated as Zn(BTZ)$_2$); 2-(4-biphenylyl)-5-(4-tert-buthylphenyl)-1,3,4-oxadiazole (abbreviated as PBD), 1,3-bis[5-(p-tert-buthylphenyl)-1,3,4-oxadiazole-2-yl]benzene (abbreviated as OXD-7), 3-(4-tert-buthylphenyl)-4-phenyl-5-(4-biphenylyl)-1,2,4-triazole (abbreviated as TAZ), 3-(4-tert-buthylphenyl)-4-(4-ethylphenyl)-5-(4-biphenylyl)-1,2,4-triazole (abbreviated as p-EtTAZ), bathophenanthroline (abbreviated as BPhen), bathocuproin (abbreviated as BCP), 4,4-bis(5-methylbenzoxazol-2-yl)stilbene (abbreviated as BzOs), or the like can be given. In addition, the electron transporting layer 114 may be formed to have a multilayer structure formed by combining two or more of layers formed of the foregoing substances.

In addition to the foregoing substances, the hole transporting layer 112 and the electron transporting layer 114 may be respectively formed of a bipolar substance. A bipolar substance refers to a substance in which a value of a ratio of one carrier mobility to the other carrier mobility is 100 or less, preferably 10 or less when carrier mobility of one of electrons and holes is compared with the other carrier's mobility. As for the bipolar substance, for example, 2,3-bis(4-diphenylaminophenyl)quinoxaline (abbreviated as TPAQn), 2,3-bis{4-[N-(1-naphthyl)-N-phenylamino]phenyl}-dibenzo[f,h]quinoxaline (abbreviated as NPADiBzQn), and the like can be given. In particular, it is preferable to use a substance of which a hole or electron mobility is $1 \times 10^{-6}$ cm$^2$/Vs or higher among bipolar substances. In addition, the hole transporting layer 112 and the electron transporting layer 114 may be formed of the same bipolar substance.

As shown in FIG. 1, the hole injecting layer 111 may be provided between the first electrode 101 and the hole transporting layer 112. The hole injecting layer 111 is a layer having a function of assisting injection of holes from the first electrode 101 to the hole transporting layer 112. By providing the hole injecting layer 111, the difference in ionization potentials between the first electrode 101 and the hole transporting layer 112 is relieved and holes become easy to be injected. The hole injecting layer 111 is preferably formed by a substance having smaller ionization potential than that of a substance which forms the hole transporting layer 112 and larger ionization potential than that of a substance which forms the first electrode 101, or a substance having an energy band which bends when the substance is formed into a thin film having a thickness of 1 to 2 nm between the hole transporting layer 112 and the first electrode 101. As a specific example of a material which can be used for forming the hole injecting layer 111, a phthalocyanine-based compound such as phthalocyanine (abbreviated as H$_2$Pc) or copper phthalocyanine (CuPc), a high molecular compound such as poly(ethylenedioxythiophene)/poly(styrenesulfonic acid) water solution (PEDOT/PSS), or the like can be given. That is, the hole injecting layer 111 can be formed by selecting a material so that ionization potential of the hole injecting layer 111 is relatively lower than that of the hole transporting layer 112.

As shown in FIG. 1, the electron injecting layer 115 may be provided between the second electrode 102 and the electron transporting layer 114. Here, the electron injecting layer 115 is a layer having a function of assisting injection of electrons from the second electrode 102 to the electron transporting layer 114. By providing the electron injecting layer 115, the difference in electron affinity between the second electrode 102 and the electron transporting layer 114 can be relieved and electrons become easy to be injected. The electron injecting layer 115 is preferably formed of a substance having higher electron affinity than that of a substance which forms the electron transporting layer 114 and lower electron affinity than that of a substance which forms the second electrode 102, or a substance having an energy band which bends when the substance is formed into a thin film having a thickness of 1 to 2 nm between the electron transporting layer 114 and the second electrode 102. As a specific example of a substance for forming the electron injecting layer 115, an inorganic material such as alkali metal, alkaline earth metal, alkali metal fluoride, alkaline earth metal fluoride, alkali metal oxide, or alkaline earth metal oxide can be given. In addition to the inorganic material, a substance which can be used to form the electron transporting layer 114 such as BPhen, BCP, p-EtTAZ, TAZ, or BzOs can also be used as a substance for forming the electron injecting layer 115 by being selected appropriately. That is, the electron injecting layer 115 can be formed by selecting a substance so that electron affinity of the electron injecting layer 115 is relatively higher than that of the electron transporting layer 114.

In the foregoing light emitting element of the present invention, each of the hole injecting layer 111, the hole transporting layer 112, the light emitting layer 113, the electron transporting layer 114, and the electron injecting layer 115 can be formed by any one of a vapor deposition method, an ink jetting method, and a coating method.

A hole generating layer may be provided instead of the hole injecting layer 111 or an electron generating layer may be provided instead of the electron injecting layer 115.

Here, the hole generating layer is a layer for generating holes. The hole generating layer can be formed by mixing at least one substance selected from substances having higher mobility of holes than that of electrons and a bipolar substance with a substance which has an electron accepting property with respect to the foregoing substances. As a substance having higher mobility of holes than that of electrons, a substance similarly to a substance which can be used to form the hole transporting layer 112 can be used. As a bipolar substance, the above mentioned bipolar substances such as TPAQn can be used. In particular, a substance including a triphenylamine in a skeleton is preferably used among substances having higher mobility of holes than that of electrons and the bipolar substance. Holes become easy to be generated by using the substance including triphenylamine in its skeleton. As a substance having an electron accepting property, metal oxide such as molybdenum oxide, vanadium oxide, ruthenium oxide, or rhenium oxide is preferably used. In such a hole generating layer, increase in film thickness does not cause increase in driving voltage; therefore, an optical design which utilizes a microcavity effect and a light interference effect are possible by adjusting the thickness of the hole generating layer. Therefore, a light emitting element with high quality which has favorable color purity and a little color change due to a viewing angle. In addition, a film thickness can be set so as to prevent short circuit of the first electrode 101 and the second electrode 102 due to affection of minute residue remaining on the surface of the electrode or unevenness of the first electrode 101 generated when the first electrode 101 is formed.

The electron generating layer is a layer for generating electrons. The electron generating layer can be formed by mixing at least one substance selected from a substance having higher mobility of electrons than that of holes and a bipolar substance with a material which has an electron donating property with respect to the foregoing substance. As a substance selected from the substances having higher mobility of electrons than that of holes, a substance similar to the substance which can be used to form the electron transporting layer 114 can be used. As a bipolar substance, the foregoing bipolar substance such as TPAQn can be used. As the material having an electron donating property, a substance selected from an alkali metal and an alkaline earth metal, such as, lithium (Li), calcium (Ca), sodium (Na), potassium (Ka), or magnesium (Mg) can be used. At least one substance selected from alkali metal oxide, alkaline earth metal oxide, alkali metal nitride, and alkaline earth metal nitride such as lithium oxide ($Li_2O$), calcium oxide (CaO), sodium oxide ($Na_2O$), potassium oxide ($K_2O$), or magnesium oxide (MgO) can be used as a substance having an electron donating property. In addition, fluoride such as alkali metal fluoride, and alkaline earth metal fluoride, such as lithium fluoride (LiF), cesium fluoride (CsF), and calcium fluoride ($CaF_2$) can be used.

The light emitting element of the present invention as described above can emit red phosphorescence with good spectral luminous efficiency which is closer to the red chromaticity coordinates according to the NTSC standard since it uses the organometallic complex of the present invention. Further, the light emitting element of the present invention has good light emission efficiency since it can emit phosphorescence.

Embodiment Mode 4

A light emitting element of the present invention may have a plurality of light emitting layers. For example, white light emission can be obtained by providing a plurality of light emitting layers and mixing light emission from respective light emitting layers. In this embodiment mode, such a light emitting element is explained with reference to FIGS. 2 and 3.

Figure 2:
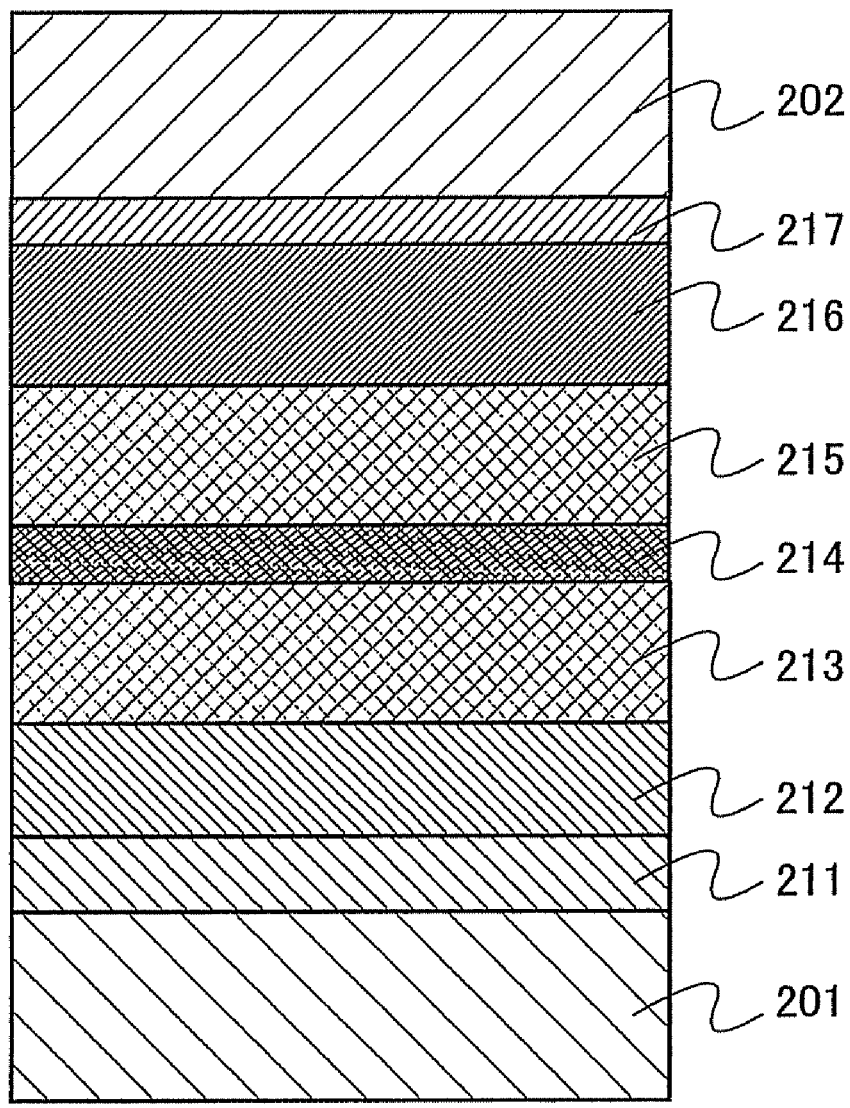
FIG. 2 is an element structure of a light emitting element of the present invention.

In FIG. 2, a first light emitting layer 213 and a second light emitting layer 215 are provided between a first electrode 201 and a second electrode 202. A partition layer 214 is preferably provided between the first light emitting layer 213 and the second light emitting layer 215.

When applying voltage so that electric potential of the second electrode 202 is higher than that of the first electrode 201, current flows between the first electrode 201 and the second electrode 202, and holes and electrons are recombined with each other within the first light emitting layer 213, the second light emitting layer 215, or the partition layer 214. Excitation energy generated in the partition layer 214 by recombination is transferred the partition layer 214 to each of the first light emitting layer 213 and the second light emitting layer 215, so that a first light emitting substance contained in the first light emitting layer 213 and a second light emitting substance contained in the second light emitting layer 215 are excited. The excited first and second light emitting substances emit light while returning to ground states.

The first light emitting layer 213 contains a first light emitting substance as typified by a fluorescent substance such as parylene, 2,5,8,11-tetra-tert-butylperylene (abbreviated as TBP), 4,4'-bis[2-diphenylvinyl]biphenyl (abbreviated as DPVBi), 4,4'-bis[2-(N-ethylcarbazol-3-yl)vinyl]biphenyl (abbreviated as BCzVBi), bis(2-methyl-8-quinolinolato)-4-phenylphenolato-aluminum (abbreviated as BAlq), and bis (2-methyl-8-quinolinonato)-chlorogallium (abbreviated as $Gamq_2Cl$); or a phosphorescent substance such as bis[2-(3,5-bis(trifluoromethyl)phenyl)pyridinato-N,$C^{2'}$]iridium(III) picolinate (abbreviated as $Ir(CF_3ppy)_2(pic)$), bis[2-(4,6-difluorophenyl(pyridinato-N,$C^{2'}$]iridium(III)acetylacetonate (abbreviated as FIr(acac)), and bis[2-(4,6-difluorophenyl)pyridinato-N,$C^{2'}$]iridium(III)picolinate (abbreviated as FIr (pic)). The first light emitting layer 213 exhibits light emission having a peak at 450 to 510 nm in an emission spectrum. The second light emitting layer 215 has the organometallic complex represented by any one of the general formulae (1) to (3) of the present invention so as to serve as a second light emitting substance and exhibits red phosphorescence with good spectral luminous efficiency which is closer to the red chromaticity coordinates according to the NTSC standard. Light emission generated in the first light emitting layer 213 and Light emission generated in the second light emitting layer 215 are emitted to outside through either or both of the first electrode 201 and the second electrode 202. Each light emission emitted to outside is mixed with each other visually and is visible as white light emission.

The first light emitting layer 213 is preferably formed by dispersing a light emitting substance which can emit light at 450 to 510 nm into a layer formed by a substance having a larger energy gap (a first host) than that of the light emitting substance, alternatively, the first light emitting layer 213 is formed by a layer formed of a light emitting substance which can emit light at 450 to 510 nm. As the first host, in addition to NPB, CBP, TCTA, Znpp$_2$, and ZnBOX; 9,10-di(2-naphthyl)anthracene (abbreviated as DNA), 9,10-di(2-naphthyl)-2-tert-buthylanthracence (abbreviated as t-BuDNA), or the like can be used. The second light emitting layer 215 is preferably formed by dispersing the organometallic complex of the present invention into a layer formed of a substance having a larger energy gap (a second host) than that of the organometallic complex of the present invention. As the second host, TPAQn, NPB, CBP, TCTA, Znpp$_2$, ZnBOX, Alq$_3$, or the like can be used. The partition layer 214 is preferably formed to have functions of transferring energy generated by recombination in the first light emitting layer 213, the second light emitting layer 215, or the partition layer 214 to both the first light emitting layer 213 and the second light emitting layer 215 and preventing the energy from transferring to either of the first light emitting layer 213 or the second light emitting layer 215. Specifically, the partition layer 214 can be formed of TPAQn, NPB, CBP, TCTA, Znpp$_2$, ZnBOX, or the like. Thus, a problem that white, light emission cannot be obtained because light intensity of only either of the first light emitting layer 213 or the second light emitting layer 215 is increased can be prevented by providing the partition layer 214.

A light emitting substance contained in the first light emitting layer 213 is not particularly limited.

In addition, as shown in FIG. 2, an electron transporting layer 212 and an electron injecting layer 211 may be formed between the first light emitting layer 213 and the first electrode 201. In addition, a hole transporting layer 216 and a hole injecting layer 217 may be formed between the second light emitting layer 215 and the second electrode 202. Note that the substances described in Embodiment Mode 3 can be used for forming these layers.

The light emitting element including two light emitting layers as shown in FIG. 2 is described in this embodiment mode; however, the number of light emitting layers is not limited to two. For example, three light emitting layers can be formed. Light emissions from the light emitting layers are mixed with each other to make visible white light emission.

Figure 3:
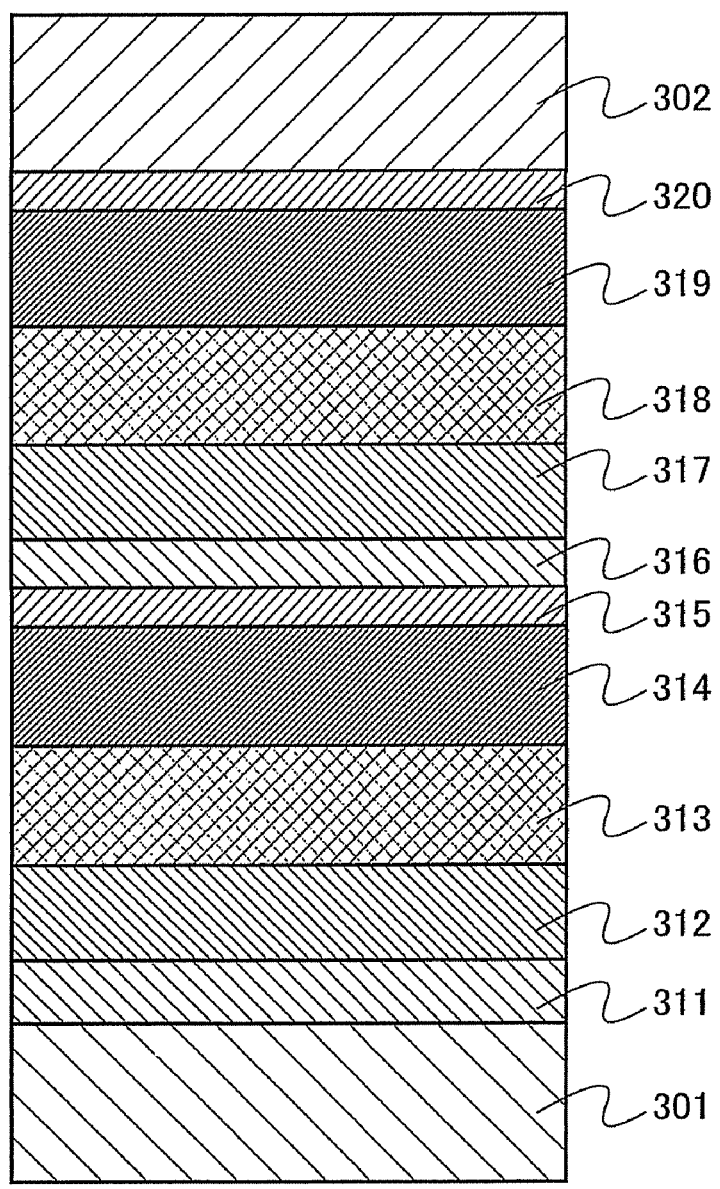
FIG. 3 is an element structure of a light emitting element of the present invention.

Alternatively, a light emitting element as shown in FIG. 3 can be formed in stead of the light emitting element described with reference to FIG. 2. The light emitting element shown in FIG. 3 has a first light emitting layer 313 and a second light emitting layer 318 between a first electrode 301 and a second electrode 302, and has a first layer 315 and a second layer 316 between the first light emitting layer 313 and the second light emitting layer 318.

The first layer 315 is a layer for generating holes, whereas the second layer 316 is a layer for generating electrons. When applying voltage so that electric potential of the second electrode 302 is higher than that of the first electrode 301, electrons injected from the first electrode 301 and holes injected from the first layer 315 are recombined with each other within the first light emitting layer 313, and a light emitting substance contained in the first light emitting layer 313 emits light. Moreover, holes injected from the second electrode 302 and electrons injected from the second layer 316 are recombined with each other within the second light emitting layer 318 and a light emitting substance contained in the second light emitting layer 318 emits light.

The first light emitting layer 313 contains a light emitting substance as typified by a fluorescent substance such as parylene, TBP, DPVBi, BCzVBi, BAlq, and Gamq$_2$Cl, or phosphorescent material such as Ir(CF$_3$ppy)$_2$(pic), FIr(acac), and FIr(pic), and emits light having a peak at 450 to 510 nm in an emission spectrum. The second light emitting layer 318 has the organometallic complex of the present invention so as to serve as a light emitting substance and exhibits red phosphorescence with good spectral luminous efficiency which is closer to the red chromaticity coordinates according to the NTSC standard. Light emissions from the first light emitting layer 313 and the second light emitting layer 318 are emitted from either or both the first electrode 301 and the second electrode 302. Light emissions from both of the light emitting layers are visually mixed and are visible as white light emission.

In the second light emitting layer 318, it is preferable that the organometallic complex is dispersedly contained in the second host as described above. Similarly, in the first light emitting layer 313, it is preferable that the light emitting substance is dispersedly contained in the above mentioned first host.

The first layer 315 is preferably a layer containing a substance which has a higher transporting property of holes than that of electrons and which contains a substance having an electron accepting property to the substance. As a substance having a higher transporting property of holes than that of electrons, a similar substance to the foregoing substances used for forming a hole transporting layer may be used. As a substance having an electron accepting property to the substance having a higher transporting property of holes than that of electrons, molybdenum oxide, vanadium oxide, 7,7,8,8-tetracyanoquinodimethane (abbreviated as TCNQ), 2,3,5,6-tetrafluoro-7,7,8,8-tetracyanoquinodimethane (abbreviated as F$_4$-TCNQ), or the like can be used.

The second layer 316 is preferably a layer containing a substance which has a higher transporting property of electrons than that of holes and which contains a substance having an electron donating property to the substance. As a substance having a higher transporting property of electrons than that of holes, a similar substance to the foregoing substances used for forming an electron transporting layer may be used. As a substance having an electron donating property to the substance having a higher transporting property of electrons than that of holes, an alkali metal such as lithium or cesium, an alkaline earth metal such as magnesium or calcium, or a rare earth metal such as erbium or ytterbium can be used.

In addition, as shown in FIG. 3, an electron transporting layer 312 and an electron injecting layer 311 may be formed between the first light emitting layer 313 and the first electrode 301. In addition, a hole transporting layer 314 may be formed between the first light emitting layer 313 and the first layer 315. In addition, a hole transporting layer 319 and a hole injecting layer 320 may be formed between the second light emitting layer 318 and the second electrode 302. In addition, an electron transporting layer 317 may be formed between the second light emitting layer 318 and the second layer 316.

The light emitting element including two light emitting layers is described as shown in FIG. 3 in this embodiment mode; however, the number of light emitting layers is not limited to two. For example, the light emitting layer can be formed of three layers. Light emissions from the light emitting layers are mixed with each other to make visible white light emission.

Embodiment Mode 5

A mode of a light emitting element using an organometallic complex of the present invention as a sensitizer is described with reference to FIG. 4.

Figure 4:
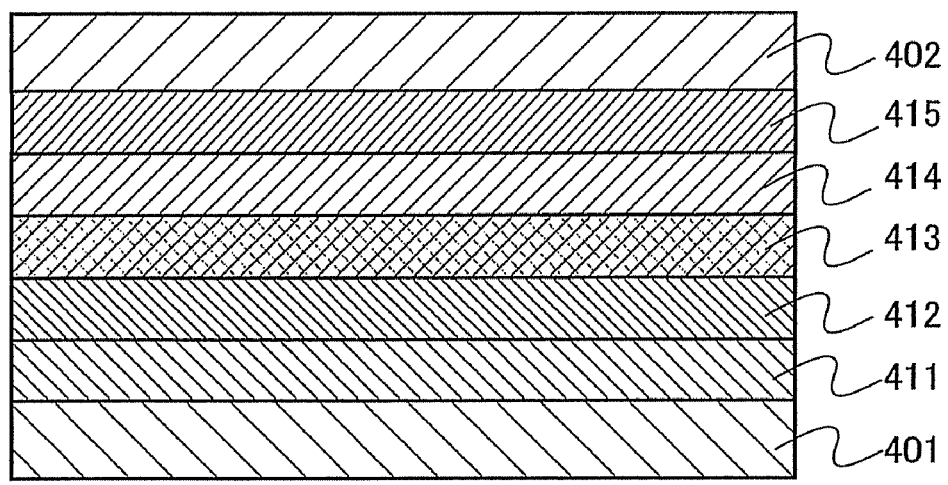
FIG. 4 is an element structure of a light emitting element of the present invention.

FIG. 4 shows a light emitting element having a light emitting layer 413 between a first electrode 401 and a second electrode 402. The light emitting layer 413 contains the organometallic complex of the present invention represented by any one of the general formulae (1) to (3), and a fluorescent material capable of emitting longer wavelength emission than that of the organometallic complex of the present invention. Note that a fluorescent material is a substance which emits light while returning from an excited state to a ground state.

In such a light emitting element, holes injected from the first electrode 401 and electrons injected from the second electrode 402 are recombined with each other within the light emitting layer 413 to excite the fluorescent material. The excited fluorescent material emits light while returning to a ground state. At this time, the organometallic complex of the present invention serves as a sensitizer for the fluorescent material to increase the number of fluorescent materials in a singlet excited state. As described above, a light emitting element with good light emission efficiency can be obtained by using the organometallic complex of the present invention as a sensitizer. In the light emitting element of this embodiment mode, the first electrode 401 serves as an anode, whereas the second electrode 402 serves as a cathode.

Although the light emitting layer 413 is not particularly limited, the light emitting layer 413 is preferably a layer formed by dispersing the organometallic complex of the present invention and the fluorescent material into a layer formed of a substance (host) having a larger energy gap than that of the organometallic complex of the present invention.

The fluorescent material is not particularly limited and a compound exhibiting light of red to infrared light such as magnesium phthalocyanine or phthalocyanine is preferably used. In addition, a substance which is used to disperse the organometallic complex of the present invention and the fluorescent material is not particularly limited. A substance or the like which can be used to disperse the organometallic complex of the present invention as described in Embodiment Mode 3 can be used.

The first electrode 401 and the second electrode 402 are not particularly limited. Similar electrodes to the first electrode 101 and the second electrode 102 described in Embodiment Mode 3 can be used.

As shown in FIG. 4, a hole injecting layer 411, a hole transporting layer 412, and the like can be provided between the first electrode 401 and the light emitting layer 413. An electron transporting layer 414, an electron injecting layer 415, and the like can be provided between the second electrode 402 and the light emitting layer 413.

The hole injecting layer 411, the hole transporting layer 412, the electron transporting layer 414, and the electron injecting layer 415 can be formed by similar layers to the hole injecting layer 111, the hole transporting layer 112, the electron transporting layer 114, and the electron injecting layer 115, respectively. Other functional layers having different functions from those of the hole injecting layer 411, the hole transporting layer 412, the electron transporting layer 414, and the electron injecting layer 415 can be provided.

The foregoing light emitting element is obtained by using the organometallic complex of the present invention as a sensitizer.

Embodiment Mode 6

Figure 5A:
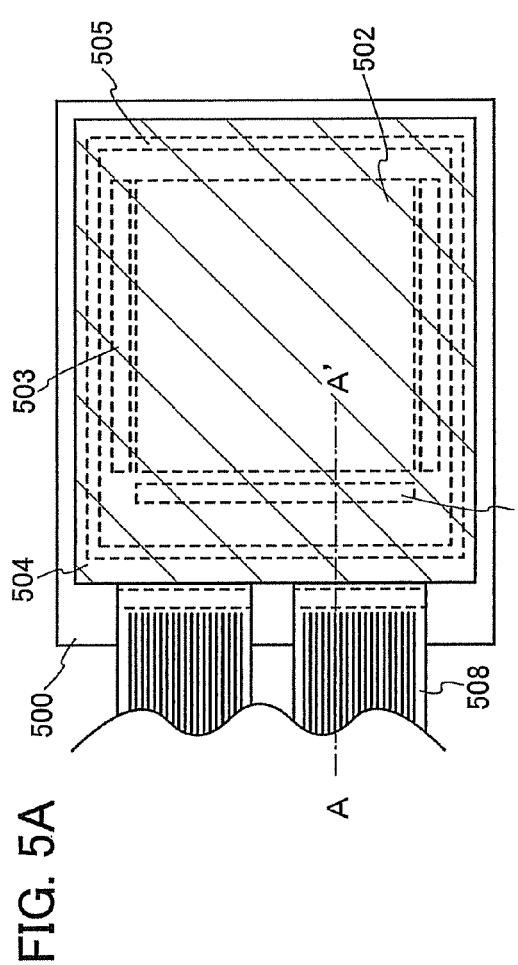
FIGS. 5A and 5B are views of a light emitting device using a light emitting element of the present invention.
Figure 5B:
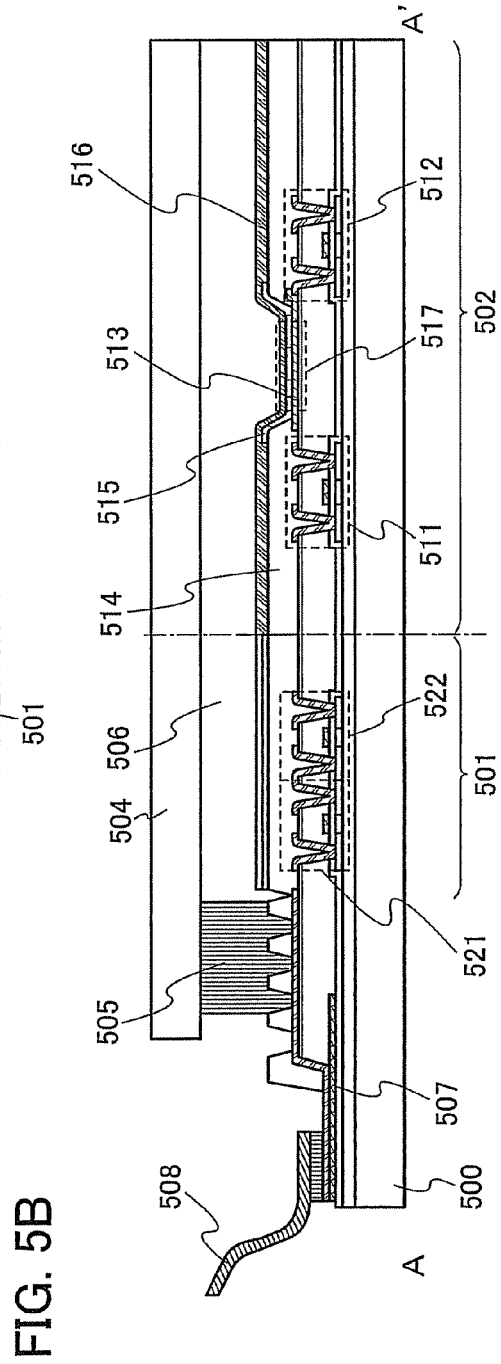

In this embodiment mode, a light emitting device to which the present invention is applied is described with reference to FIGS. 5A and 5B. Note that FIG. 5A is a top view showing the light emitting device and FIG. 5B is a cross-sectional view of FIG. 5A taken along the line A-A'. In FIGS. 5A and 5B, the same reference numeral is used for the similar portions. Reference numeral 500 denotes a substrate. Reference numeral 501 indicated by a dashed line denotes a driver circuit portion (a source side driver circuit); 502, a pixel portion; and 503, a driver circuit portion (a gate side driver circuit). Reference numeral 504 denotes a sealing substrate, reference numeral 505 indicated by a dashed line denotes a sealant, and a portion surrounded by the sealant 505 is a space 506.

Note that 507 denotes a wire for transmitting a signal to be inputted to the source side driver circuit 501 or the gate side driver circuit 503 and receives a video signal, a clock signal, a start signal, a reset signal, or the like from an FPC 508 (flexible printed circuit) 508 that is an external input terminal. Note that only the FPC is shown here; however, the FPC 508 may be provided with a printed wiring board (PWB). The light emitting device of the present invention includes not only a light emitting device itself but also a light emitting device with an FPC or a PWB attached thereto.

Subsequently, a cross-sectional structure is described with reference to FIG. 5B. The driver circuit portion and the pixel portion 502 are formed over the substrate 500. Here, the source side driver circuit 501 which is the driver circuit portion and the pixel portion 502 are shown.

Note that a CMOS circuit which is a combination of an n-channel thin film transistor 521 and a p-channel thin film transistor 522 is formed in the source side driver circuit 501. A thin film transistor for forming the driver circuit may be formed using a known CMOS circuit, a PMOS circuit, or an NMOS circuit. A driver integration type in which a driver circuit is formed over a substrate is described in this embodiment mode, but it is not necessarily required to be a driver integration type and a driver circuit can be formed outside a substrate.

The pixel portion 502 includes a plurality of pixels, each of which includes a switching thin film transistor 511, a current control thin film transistor 512, and a first electrode 513 which is electrically connected to a drain of the current control thin film transistor 512. Note that an insulator 514 is formed to cover an end of the first electrode 513.

The insulator 514 is preferably formed so as to have a curved surface with a curvature at an upper end and/or a lower end thereof in order to make the deposition of a layer containing a light emitting substance 515 which is formed later favorable. For example, in the case of using positive type photosensitive acrylic as a material for the insulator 514, the insulator 514 is preferably formed to have a curved surface with a curvature radius (0.2 to 3 μm) only at the upper end. Either a negative type which becomes insoluble in an etchant by light irradiation or a positive type which becomes soluble in an etchant by light irradiation can be used as the insulator 514. In addition, as a material for the insulator 514, not only an organic material but also an inorganic material such as silicon oxide, or silicon oxynitride can be used.

The layer containing a light emitting substance 515 and a second electrode 516 are formed over the first electrode 513.

A light emitting element 517 including the first electrode 513, the layer containing a light emitting substance 515, and the second electrode 516 is a light emitting element having the organometallic complex of the present invention. As long as the layer containing a light emitting substance 515 has a light emitting layer which contains at least one of the organometallic complexes represented by the general formulae (1) to (3), a stacked-layer structure of other layers are not particularly limited. Note that each of the first electrode 513, the layer containing a light emitting substance 515, and the second electrode 516 can be formed of a material which is appropriately selected from those described in Embodiment Mode 3.

By attaching the sealing substrate 504 to the substrate 500 with the sealant 505, a light emitting element 517 is provided in the space 506 surrounded by the substrate 500, the sealing substrate 504, and the sealant 505. Note that the space 506 may be filled with the sealant 505 or may be filled with an inert gas (nitrogen, argon, or the like).

An epoxy-based resin is preferably used as the sealant 505. The material preferably allows as little moisture and oxygen as possible to penetrate. As the sealing substrate 504, a plastic substrate formed of FRP (Fiberglass-Reinforced Plastics), PVF (polyvinyl fluoride), myler, polyester, acrylic, or the like can be used in addition to a glass substrate or a quartz substrate. As described above, a light emitting device can be formed.

When both the first electrode 513 and the second electrode 516 are formed of a substance having a light transmitting property, light can be extracted through both the first electrode 513 and the second electrode 516. When only the second electrode 516 is formed of a substance having a light transmitting property, light can be extracted only from the second electrode 516. In this case, it is preferable that the first electrode 513 is formed of a material with high reflectance, or a film formed of a material with high reflectance (reflection film) is provided under the first electrode 513. When only the first electrode 513 is formed of a material having a light transmitting property, light can be extracted only from the first electrode 513. In this case, the second electrode 516 is preferably formed of a material with high reflectance or a reflection film is preferably provided over the second electrode 516.

In the light emitting element 517, the layer containing a light emitting substance 515 may be stacked so that the light emitting element 517 operates when applying voltage so that the potential of the second electrode 516 is higher than that of the first electrode 513. Alternatively, in the light emitting element 517, the layer containing a light emitting substance 515 may be stacked so that the light emitting element 517 when applying voltage so that the potential of the second electrode 516 is lower than that of the first electrode 513.

The light emitting device of the present invention has good spectral luminous efficiency since it has an organometallic complex of the present invention as a light emitting substance. In addition, since the light emitting device can emit red phosphorescence which is closer to the red chromaticity coordinates according to the NTSC standard, red chromaticity coordinates in a sending side from which a signal conforming to the NTSC standard is transmitted to a driver circuit and those in a receiving side which exhibits light emission are almost identical. Therefore, a display device with accurate color reproducibility with respect to inputted image information can be obtained.

As described above, an active light emitting device in which drive of a light emitting element is controlled by a transistor is explained in this embodiment mode. However, a passive light emitting device in which the light emitting element is driven without particularly providing a driving element such as a thin film transistor in each pixel may also be employed.

Note that this embodiment mode can be freely combined with Embodiment Modes 1 to 5 and the following Example 1.

Embodiment Mode 7

Figure 11A:
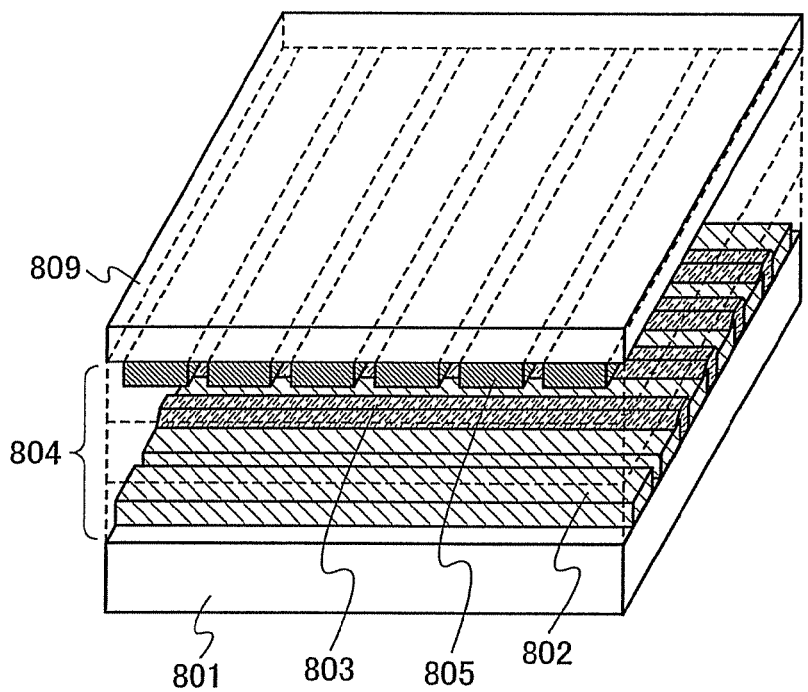
FIGS. 11A and 11B are views of a light emitting device using a light emitting element of the present invention.
Figure 11B:
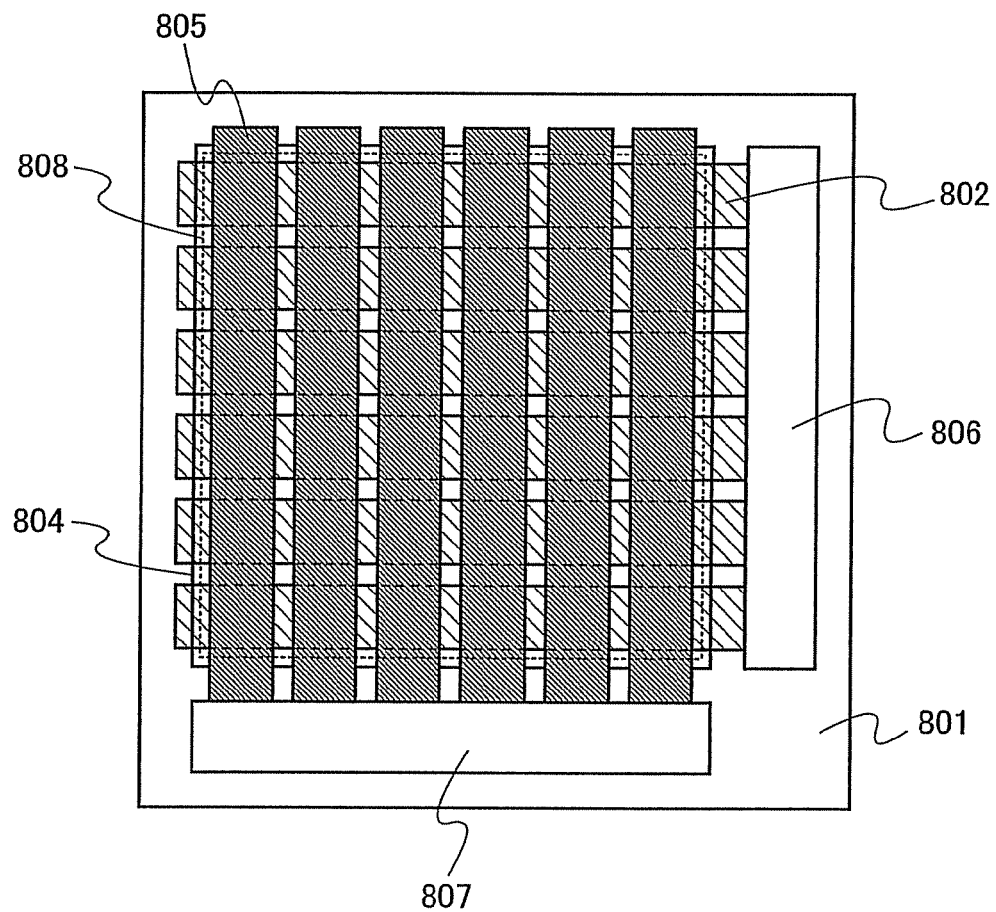

In this embodiment mode, a passive light emitting device to which the present invention is applied is described with reference to FIGS. 11A and 11B. FIGS. 11A and 11B show a perspective view and a top view of the passive light emitting device to which the present invention is applied, respectively. Note that FIG. 11A is a perspective view of a portion surrounded by a dashed line 808 in FIG. 11B. In FIGS. 11A and 11B, the same reference numeral is used for the same portions. In FIG. 11A, a plurality of first electrodes 802 is formed in parallel with one another over the first substrate 801. Each edge portion of the first electrodes 802 is covered with a partition layer 803. The frontmost first electrode 802 also has an edge portion covered with the partition layer 803, although which is not shown in FIG. 11A for a simpler description of a manner in which the plurality of first electrodes 802 and the partition layers 803 are arranged over the first substrate 801. A plurality of second electrodes 805 is formed over the first electrodes 802 in parallel with one another so as to intersect with the first electrodes 802. A layer containing a light emitting substance 804 is faulted between the first electrodes 802 and the second electrodes 805. A portion in which the first electrode 802 and the second electrode 805 intersect forms a light emitting element of the present invention in which the layer containing a light emitting substance 804 is interposed between the electrodes. As long as the layer containing a light emitting substance 804 has a light emitting layer which contains at least one of the organometallic complexes represented by the general formulae (1) to (3), a stacked-layer structure of other layers are not particularly limited. Note that each of the first electrodes 802, the layer containing a light emitting substance 804, and the second electrodes 805 can be formed of a material which is appropriately selected from those described in Embodiment Mode 3. A second substrate 809 is formed over the second electrodes 805.

As shown in FIG. 11B, the first electrodes 802 are connected to a first, driver circuit 806 and the second electrodes 805 are connected to a second driver circuit 807. A light emitting element of the present invention selected according to a signal from the first driver circuit 806 and the second driver circuit 807 emits light. The light is extracted outside through the first electrodes 802 and/or the second electrodes 805. Light emissions from a plurality of the light emitting elements are combined with each other to display an image. Note that in FIG. 11B, the partition layers 803 and the second substrates 809 are not shown for a simpler description of arrangement of the first electrodes 802 and the second electrodes 805.

When both the first electrodes 802 and the second electrodes 805 are formed of a substance having a light transmitting property, light can be extracted through both the first electrodes 802 and the second electrodes 805. When only the second electrodes 805 are formed of a substance having a light transmitting property, light can be extracted only from the second electrodes 805. In this case, it is preferable that the first electrodes 802 is formed of a material with high reflectance, or a film formed of a material with high reflectance (reflection film) is provided under the first electrodes 802. When only the first electrodes 802 are formed of a substance having a light transmitting property, light can be extracted only from the first electrodes 802. In this case, the second electrodes 805 are preferably formed of a material with high reflectance or a reflection film is preferably provided over the second electrodes 805. The partition layers 803 can be formed of a material similar to that of the insulator 514 described in Embodiment Mode 6.

The light emitting device of the present invention has good spectral luminous efficiency since it has an organometallic complex of the present invention as a light emitting substance. In addition, since the light emitting device can emit red phosphorescence which is closer to the red chromaticity coordinates according to the NTSC standard, red chromaticity coordinates in a sending side from which a signal conforming to the NTSC standard is transmitted to a driver circuit and those in a receiving side which exhibits light emission are almost identical. Therefore, a display device with accurate color reproducibility with respect to inputted image information can be obtained.

Note that this embodiment mode can be freely combined with Embodiment Modes 1 to 5 and the following Example 1.

Embodiment Mode 8

In this embodiment mode, various electronic appliances which are accomplished by using a light emitting device having a light emitting element of the present invention are described. The organometallic complex in the light emitting element of the present invention can emit red phosphorescence with good spectral luminous efficiency which is closer to the red chromaticity coordinates according to the NTSC standard. Therefore, the light emitting device of the present invention has good spectral luminous efficiency. In addition, since red chromaticity coordinates in a sending side from which a signal conforming to the NTSC standard is transmitted to a driver circuit and those in a receiving side which exhibits light emission are almost identical, a display device with accurate color reproducibility with respect to inputted image information can be obtained.

As an electronic appliance manufactured using a light emitting device of the present invention, a television, a camera such as a video camera or a digital camera, a goggle type display (head mounted display), a navigation system, an audio reproducing device (such as a car audio and an audio component stereo), a notebook personal computer, a game machine, a portable information terminal (such as a mobile computer, a portable phone, a portable game machine, and an electronic book), an image reproducing device provided with a recording medium (specifically, a device for reproducing a recording medium such as a digital video disc (DVD) and having a display device for displaying the reproduced image) and the like. FIGS. 6A to 6E show specific examples of such electronic appliances. The electronic appliances using the light emitting device of the present invention is not limited to the shown specific examples.

Figure 6A:
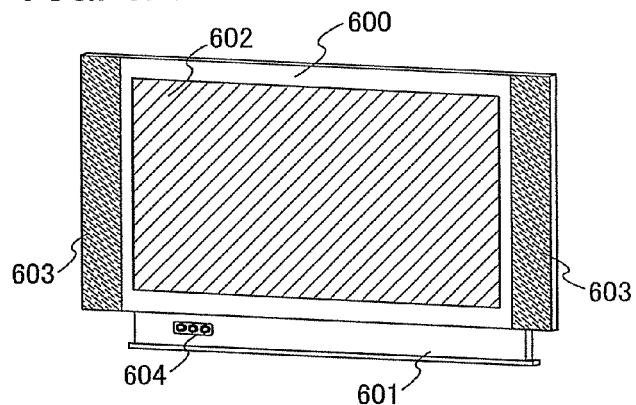
FIGS. 6A to 6E are views of electronic appliances using a light emitting element of the present invention.

FIG. 6A shows a display device including a housing 600, a support base 601, a display portion 602, a speaker portion 603, a video input terminal 604, and the like. The display device is manufactured using a light emitting device of the present invention in the display portion 602. Note that the display device includes all devices for displaying information such as for a personal computer, for receiving TV broadcasting, and for displaying an advertisement.

A light emitting element of the present invention is provided in the display portion 602. A layer containing a light emitting substance included in the light emitting element has a light-emitting layer which contains at least one of the organometallic complexes represented by the general formulae (1) to (3). Therefore, by using a light emitting element of the present invention, a display device with good spectral luminous efficiency and with accurate color reproducibility with respect to inputted image information can be obtained.

Figure 6B:
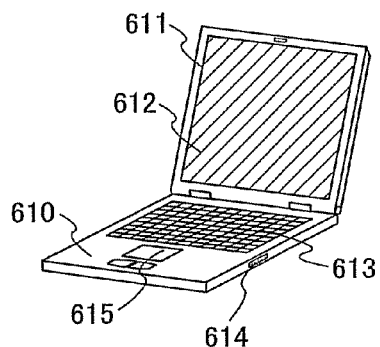

FIG. 6B shows a notebook personal computer including a main body 610, a housing 611, a display portion 612, a keyboard 613, an external connection port 614, a pointing mouse 615, and the like.

A light emitting element of the present invention is provided in the display portion 612. A layer containing a light emitting substance included in the light emitting element has a light-emitting layer which contains at least one of the organometallic complexes represented by the general formulae (1) to (3). Therefore, by using a light emitting element of the present invention, a notebook personal computer with good spectral luminous efficiency and with accurate color reproducibility with respect to inputted image information can be obtained.

Figure 6C:
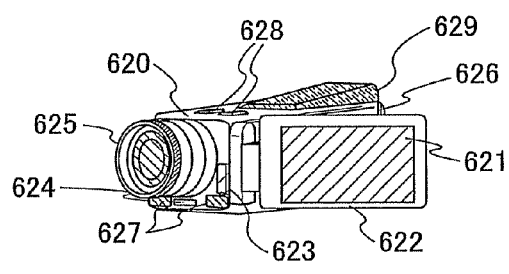

FIG. 6C shows a video camera including a main body 620, a display portion 621, a housing 622, an external connection port 623, a remote control receiving portion 624, an image receiving portion 625, a battery 626, an audio input portion 627, operation keys 628, an eyepiece portion 629, and the like.

A light emitting element of the present invention is provided in the display portion 621. A layer containing a light emitting substance included in the light emitting element has a light-emitting layer which contains at least one of the organometallic complexes represented by the general formulae (1) to (3). Therefore, by using a display device of the present invention, a video camera with good spectral luminous efficiency and with accurate color reproducibility with respect to inputted image information can be obtained.

Figure 6D:
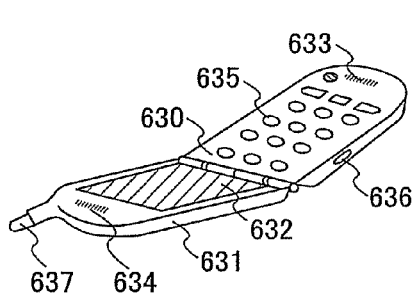

FIG. 6D shows a portable phone including a main body 630, a housing 631, a display portion 632, an audio input portion 633, an audio output portion 634, operation keys 635, an external connection port 636, an antenna 637, and the like.

A light emitting element of the present invention is provided in the display portion 632. A layer containing a light emitting substance included in the light emitting element has a light-emitting layer which contains at least one of the organometallic complexes represented by the general formulae (1) to (3). Therefore, by using a light emitting element of the present invention, a portable phone with good spectral luminous efficiency and with accurate color reproducibility with respect to inputted image information can be obtained.

Figure 6E:
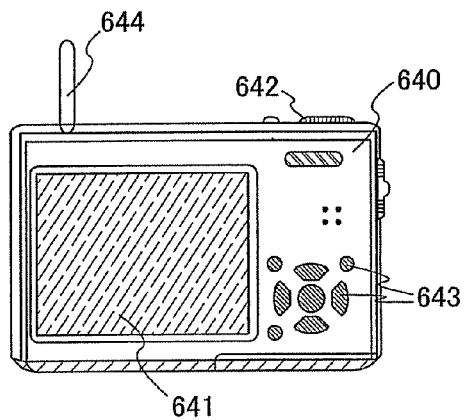

FIG. 6E shows a digital camera, including a main body 640, a display portion 641, a shutter 642, operation keys 643, an antenna 644, an imaging portion, and the like. Note that FIG. 6E shows the digital camera seen from the display portion 641 side, and the imaging portion is not shown.

The digital camera of the present invention may receive a signal such as a video signal or audio signal via the antenna 644 and the display portion 641 may serve as a display medium such as a TV receiver. Note that a speaker, an operation switch, and the like may be appropriately formed when the digital camera serves as a display medium.

A light emitting element of the present invention is provided in the display portion 641. A layer containing a light emitting substance included in the light emitting element has a light-emitting layer which contains at least one of the organometallic complexes represented by the general formulae (1) to (3). Therefore, by using a light emitting element of the present invention, a digital camera with good spectral luminous efficiency and with accurate color reproducibility with respect to inputted image information can be obtained.

As described above, the applicable range of the present invention is so wide that the present invention can be applied to display devices of various fields. In addition, the electronic appliance of this embodiment mode can be appropriately combined with any of the structures described in Embodiment Modes 1 to 7 and the following Example 1.

Example 1

A synthesis example of an organometallic complex of the present invention is described. Note that the present invention is not limited to the organometallic complex of the synthesis example described below.

Synthesis Example 1

This is a synthesis example of bis[2,3-bis(4-fluorophenyl)quinoxalinato](tetrapyrazolyl boronato)iridium(III) (abbreviated as $Ir(fdpq)_2(bpz_4)$) represented by the structural formula (5).

Step 1: Synthesis of a Ligand (Abbreviated as Hfdpq)

3.71 g of 4,4'-difluorobenzyl and 1.71 g of o-phenylenediamine were refluxed in a chloroform solvent for 6 hours. The reaction solution was cooled to room temperature, washed with 1 mol/L of hydrochloric acid and a saturated aqueous solution of sodium chloride, and dried with magnesium sulfate. The solvent was removed to obtain a ligand 2,3-bis(4-fluorophenyl)quinoxaline (abbreviated as Hfdpq) (pale yellow powder, yield: 99%). Note that recrystallization was conducted using chloroform as a solvent. The synthetic scheme (b-1) of Step 1 is shown below.

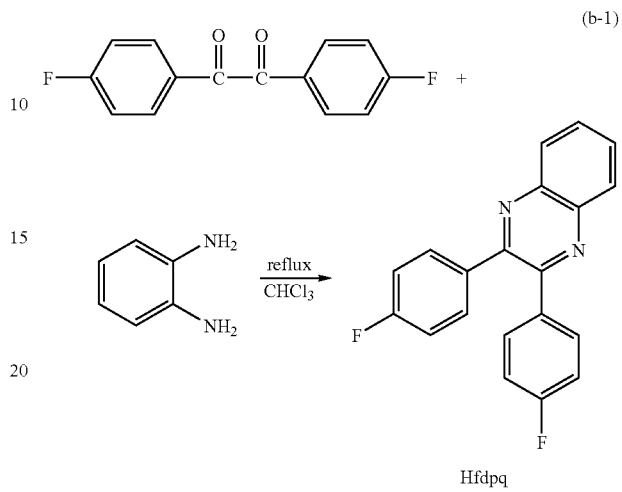

Step 2: Synthesis of a Binuclear Complex (Abbreviated as $[Ir(fdpq)_2Cl]_2$)

3.61 g of the ligand Hfdpq and 1.35 g of iridium chloride ($IrCl_3 \cdot HCl \cdot H_2O$) were mixed, with a mixture of 30 ml of 2-ethoxyethanol and 10 ml of water as a solvent and refluxed in a nitrogen atmosphere for 17 hours to obtain a binuclear complex (abbreviated as $[Ir(fdpq)_2Cl]_2$) (brown powder, yield: 99%). The synthetic scheme (b-2) of Step 2 is shown below.

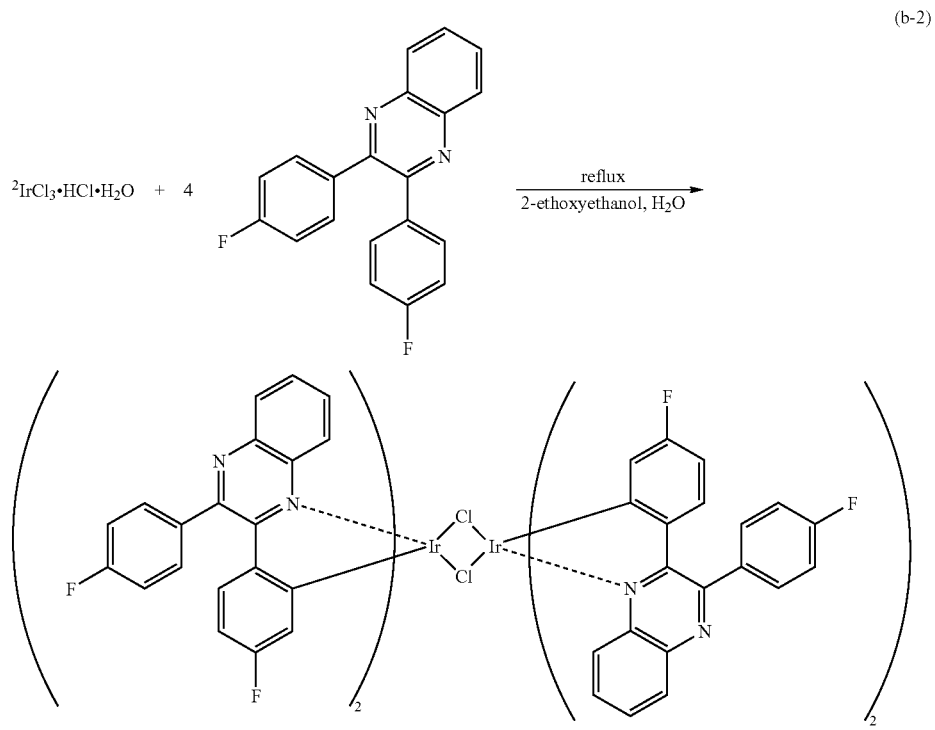

Step 3: Synthesis of an Organometallic Complex of the Present Invention (Abbreviated as Ir(fdpq)$_2$(bpz$_4$))

1.08 g of the obtained [Ir(fdpq)$_2$Cl]$_2$ was stirred in a solvent of 40 ml of dichloromethane. A solution in which 0.40 g of silver trifluoromethanesulfonate was dissolved by using 40 ml of methanol as a solvent, was dropped thereto. Then, stirring was performed at room temperature for 2 hours, the obtained suspension solution was centrifuged, and a supernatant solution obtained by the centrifugation was divided by decantation to be concentrated and dried. Furthermore, the obtained solid was mixed with 0.70 g of potassium tetrapyrazolyl boronato (abbreviated as Kbpz$_4$) by using 30 ml of acetonitrile as a solvent. Then, the mixed solution was refluxed in a nitrogen atmosphere for 18 hours to obtain the organometallic complex of the present invention, Ir(fdpq)$_2$(bpz$_4$) (red powder, yield: 51%). The synthetic scheme (b-3) of Step 3 is shown below.

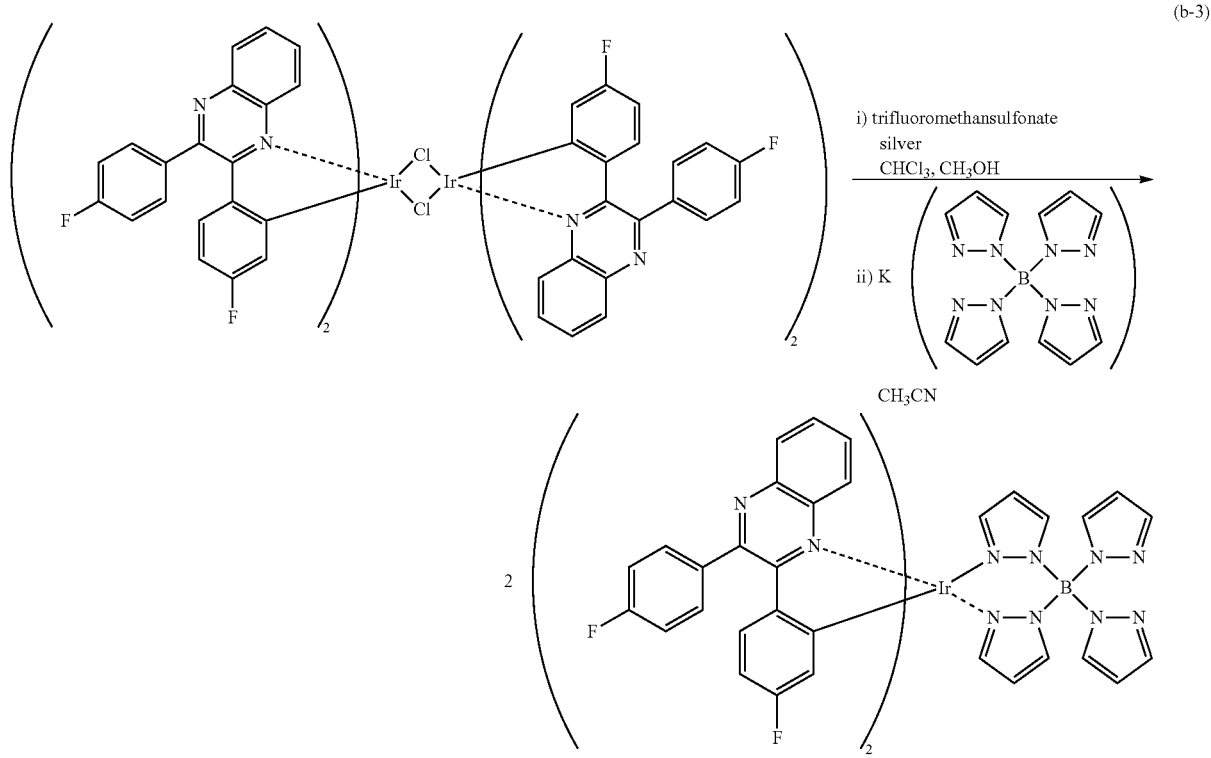

(b-3)

The obtained red powder was analyzed by nuclear magnetic resonance spectroscopy ($^1$H-NMR) and the product was identified as Ir(fdpq)$_2$(bpz$_4$) which is one of the organometallic complexes of the present invention. The result was as follows.

$^1$H-NMR. δ (CDCl$_3$): 7.95 (d, 2H), 7.75 (brs, 4H), 7.55 (t, 2H), 7.23 (m, 10H), 7.09 (m, 4H), 6.82 (sd, 2H), 6.40 (td, 2H), 6.17 (m, 6H), 5.73 (s, 2H).

Decomposition temperature $T_d$ of the obtained Ir(fdpq)$_2$(bpz$_4$) was measured by Thermo-Gravimetric/Differential Thermal Analyzer (from Seiko Instruments Inc., TG/DTA) and the result was $T_d$=334° C., which shows the obtained product has good heat resistance.

Figure 7:
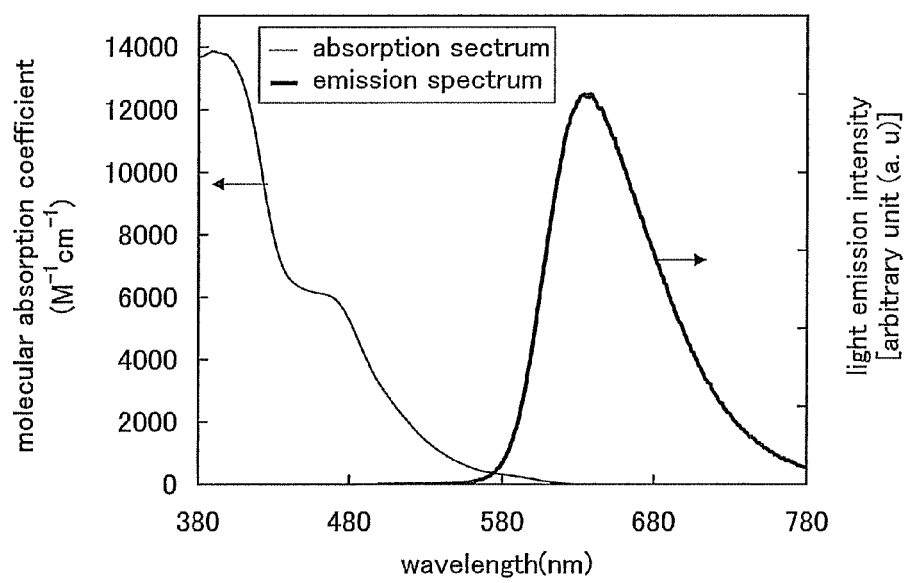
FIG. 7 shows an absorption spectrum and an emission spectrum of an organometallic complex obtained in Synthesis Example 1 in Example 1.

FIG. 7 shows an absorption spectrum and an emission spectrum (Photo Luminescence) of Ir(fdpq)$_2$(bpz$_4$) in dichloromethane. In FIG. 7, the left vertical axis indicates molecular absorption coefficient (M$^{-1}$ cm$^{-1}$), whereas the right vertical axis indicates light emission intensity [arbitrary unit (a. u)]. The emission spectrum was obtained when using light at a wavelength of 468 nm taken out by spectroscopy of halogen lamp light by slit as exciting light. As shown in FIG. 7, Ir(fdpq)$_2$(bpz$_4$), the organometallic complex of the present invention, has absorption peaks at 390 nm, 465 nm (sh), and 585 nm (sh). The emission spectrum has an emission peak at 634 nm and the emission is red emission.

The obtained Ir(fdpq)$_2$(bpz$_4$), has a plurality of absorption peaks at a long wavelength side. The peaks are absorption specific to an organometallic complex and are frequently observed in an ortho-metalated complex or the like, which may correspond to singlet MLCT (Metal to ligand charge transfer) transition, triplet π-π* transition, or triplet MLCT transition. In particular, the absorption peak on the longest-wavelength side spreads towards the bottom broadly in a visible region, which shows that the absorption spectrum is an absorption spectrum specific to triplet MLCT transition. Therefore, Ir(fdpq)$_2$(bpz$_4$), is identified as a compound capable of direct light excitation or intersystem crossing to a triplet excited state.

Further, a gas containing oxygen was injected into a dichloromethane solution containing the obtained Ir(fdpq)$_2$(bpz$_4$) to examine light emission intensity of Ir(fdpq)$_2$(bpz$_4$) with dissolved oxygen. Argon was injected into a dichloromethane solution containing the obtained Ir(fdpq)$_2$(bpz$_4$) to examine light emission intensity of Ir(fdpq)$_2$(bpz$_4$) with dissolved argon. As a result, light emission derived from the Ir(fdpq)$_2$(bpz$_4$) with dissolved oxygen was hardly observed whereas light emission derived from the Ir(fdpq)$_2$(bpz$_4$) with dissolved argon was observed. Therefore, light emission derived from Ir(fdpq)$_2$(bpz$_4$) was identified as phosphorescence.

The obtained Ir(fdpq)$_2$(bpz$_4$) can emit red phosphorescence with good spectral luminous efficiency which is closer to the red chromaticity coordinates according to the NTSC standard.

Figure 8:
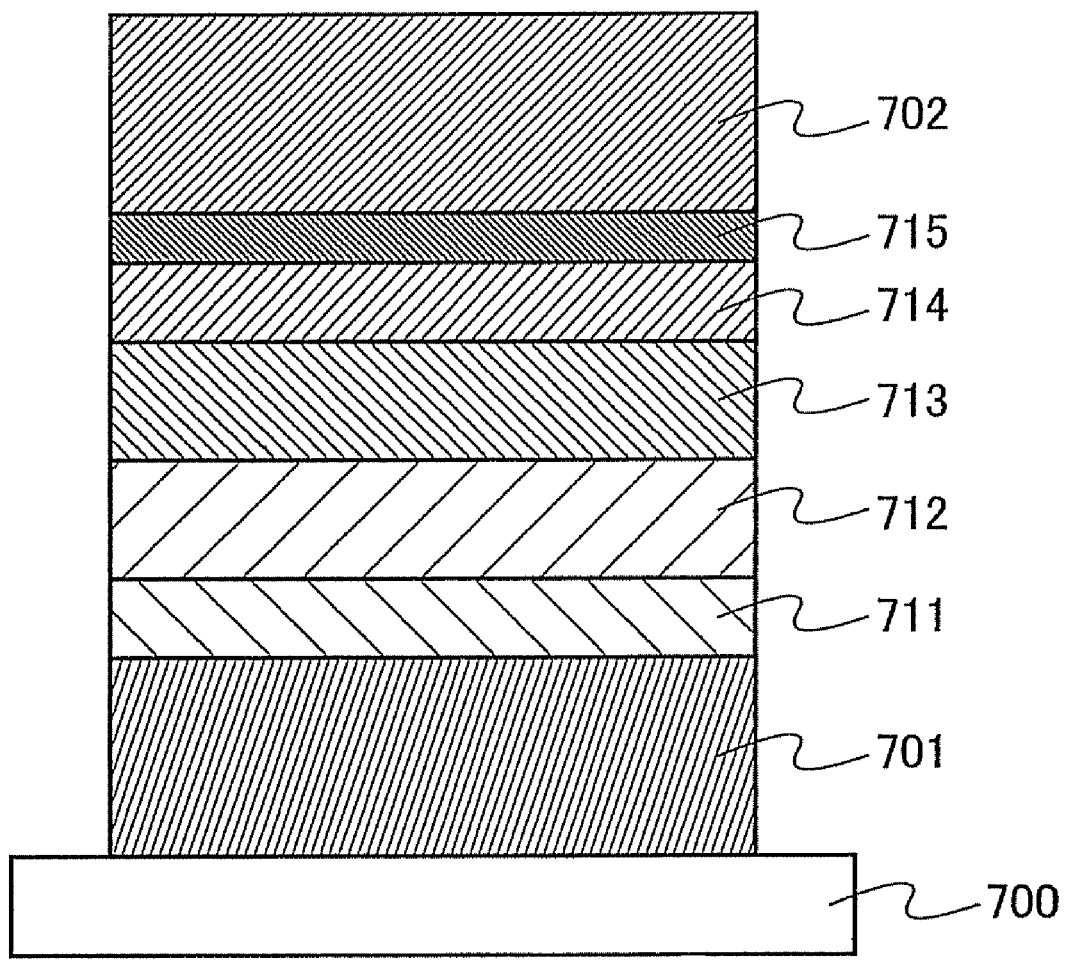
FIG. 8 is an element structure of a light emitting element manufactured in Example 1.

A light emitting element manufactured using the obtained Ir(fdpq)$_2$(bpz$_4$) is described with reference to FIG. 8.

First, a first electrode 701 was formed of ITO containing silicon oxide by a sputtering method.

Then, the substrate 700, over which the first electrode 701 was formed, was fixed to a substrate holder in a vacuum evaporation apparatus so that the side on which the first electrode 701 was formed faced downward. Then, a hole injecting layer 711 was formed of DNTPD and molybdenum trioxide by a co-evaporation method to have a thickness of 50 nm. The co-evaporation was performed so that a mass ratio of DNTPD to molybdenum oxide was 4:2 (=DNTPD:molybdenum oxide).

Then, a hole transporting layer 712 was formed of NPB by an evaporation method over the hole injecting layer 711 to have a thickness of 10 nm.

Then, a light emitting layer 713 was formed of CBP and Ir(fdpq)$_2$(bpz$_4$) by a co-evaporation method over the hole transporting layer 712 to have a thickness of 30 nm. Note that the co-evaporation was performed so that a mass ratio of CBP to Ir(fdpq)$_2$(bpz$_4$) was 1:0.08 (=CBP:Ir(fdpq)$_2$(bpz$_4$)). Therefore, Ir(fdpq)$_2$(bpz$_4$) was in a state of being dispersed in a layer formed of CBP.

An electron transporting layer 714 was formed of BCP over the light emitting layer 713 by an evaporation method to have a thickness of 10 nm.

An electron injecting layer 715 was formed of Alq$_3$ and Li by a co-evaporation method over the electron transporting layer 714 to have a thickness of 50 nm. Note that the co-evaporation was performed so that a mass ratio of Alq$_3$ to Li was 1:0.01 (=Alq$_3$:Li).

A second electrode 702 was formed of aluminum by an evaporation method over the electron injecting layer 715.

As described above, the hole injecting layer 711, the hole transporting layer 712, the light emitting layer 713, the electron transporting layer 714, and the electron injecting layer 715 were stacked between the first electrode 701 and the second electrode 702 to form a light emitting element.

Figure 9A:
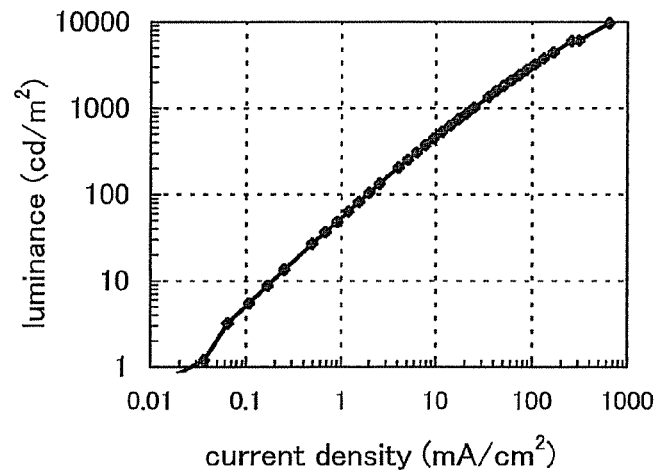
FIGS. 9A to 9C are views of operating characteristics of a light emitting element manufactured in Example 1.
Figure 9B:
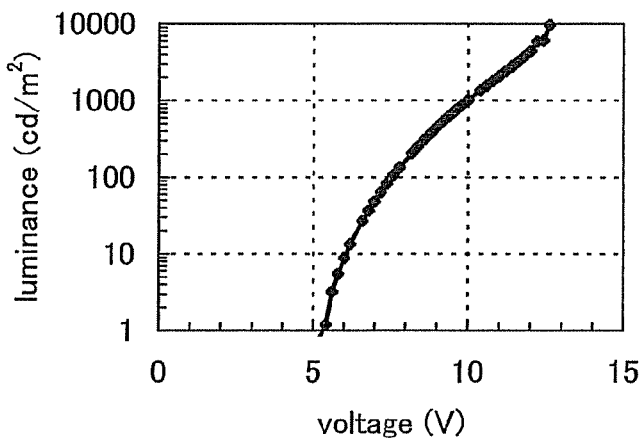
Figure 9C:
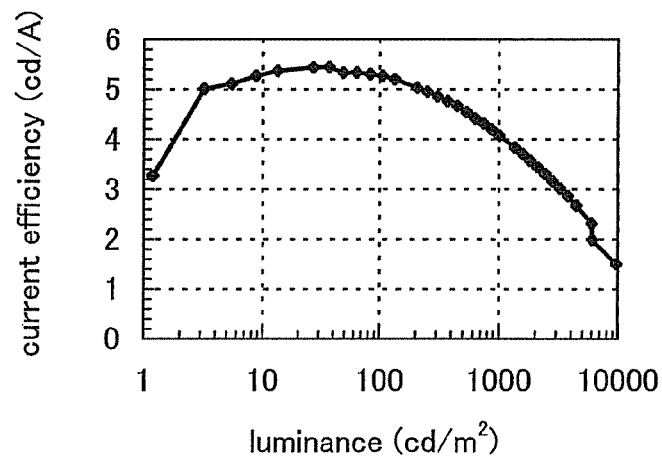

Note that the obtained light emitting element was sealed using a sealant in a nitrogen atmosphere without being exposed to atmosphere. Voltage was applied to the light emitting element described in this example so that potential of the first electrode 701 was higher than that of the second electrode 702 and operation characteristics of the light emitting element were measured. Note that the measurement was conducted at room temperature (25° C.). The result is shown in FIGS. 9A to 9C. FIG. 9A shows a current density-luminance characteristic. FIG. 9B shows a voltage-luminance characteristic. FIG. 9C shows a luminance-current efficiency characteristic. In FIG. 9A, the horizontal axis indicates a current density (mA/cm$^2$), and the vertical axis indicates luminance (cd/m$^2$). In FIG. 9B, the horizontal axis indicates voltage (V), and the vertical axis indicates luminance (cd/m$^2$). In FIG. 9C, the horizontal axis indicates luminance (cd/m$^2$), and the vertical axis indicates current efficiency (cd/A).

As a result, when a voltage of 10.0 V was applied, the light emitting element emits light with a luminance of 1000 cd/m$^2$ and current efficiency at that time was 4.1 cd/A. External quantum efficiency was 6.9%. Note that external quantum efficiency is a ratio of the number of photons emitted to outside of the element to the number of electrons injected to the light emitting element. A calculation method is shown below.

External quantum efficiency $\phi_{ext}$ can be represented by the following expression (1) wherein the number of photons per unit area is Np, the number of electrons per unit area is Ne.

$$\phi_{ext} = N_p/N_e \qquad (1)$$

Np can be represented by the following expression (2) wherein L is luminance (cd/m$^2$), I($\lambda$) is a standardized light emission spectrum in each wavelength (standardized light emission intensity in each wavelength), K($\lambda$) is a standard relative spectral luminous efficiency curve, c is light speed, and H is Plank constant.

$$N_p = \frac{\pi \cdot L}{\int I(\lambda)K(\lambda)d\lambda} \cdot \int \frac{I(\lambda)\lambda}{683 \cdot c \cdot h} d\lambda \qquad (2)$$

Ne can be represented by the following expression (3), wherein J is current density (A/m$^2$) and e is the amount of elementary electric charge (C).

$$N_e = J/e \qquad (3)$$

The following expression (4) can be obtained from the expressions (1) to (3).

$$\phi_{ext} = \frac{\pi \cdot e}{683 \cdot c \cdot h} \cdot \frac{\int I(\lambda)\lambda d\lambda}{\int I(\lambda)K(\lambda)d\lambda} \qquad (4)$$

Figure 10:
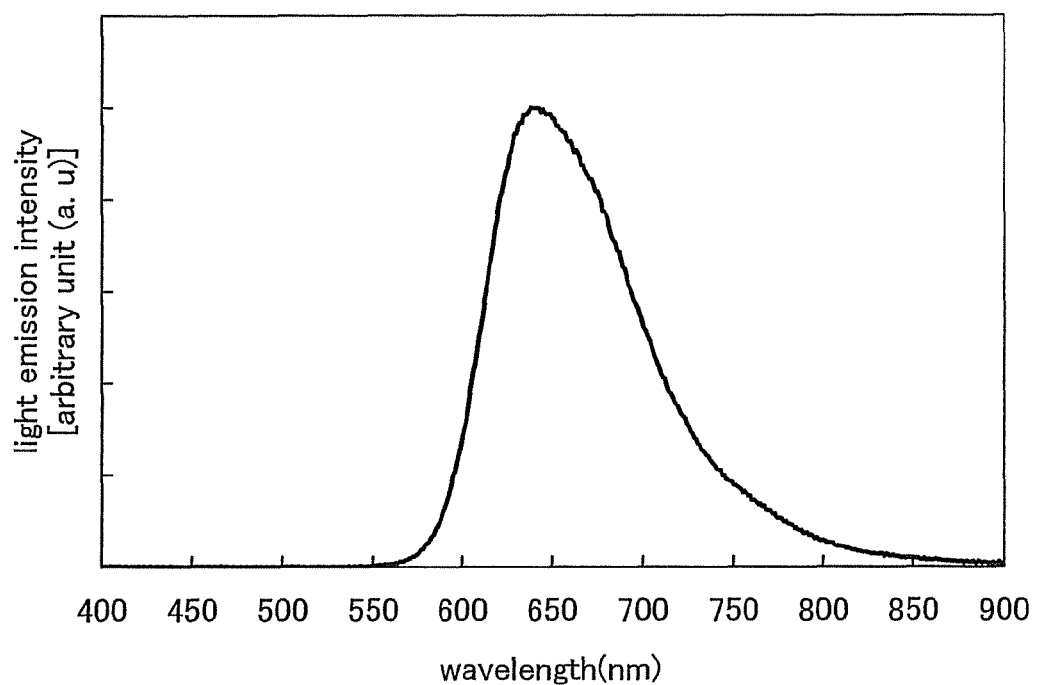
FIG. 10 is a diagram showing an emission spectrum of a light emitting element manufactured in Example 1.

Therefore, the external quantum efficiency was calculated as 6.9% from the current efficiency obtained in the above measurement and the emission spectrum shown in FIG. 10.

Note that according to FIG. 10, a peak wavelength of the emission spectrum was 638 nm and CIE chromaticity coordinates were (X, Y)=(0.69, 0.31).

Thus, by using Ir(fdpq)$_2$(bpz$_4$) as a light emitting substance, a light emitting element which exhibits red phosphorescence with good spectral luminous efficiency which was closer to the red chromaticity coordinates of the NTSC standard could be obtained. In addition, an element with high light emission efficiency could be obtained.

This application is based on Japanese Patent Application serial no. 2005-230660 filed in Japan Patent Office on Aug. 9, 2005, the entire contents of which are hereby incorporated by reference.

What is claimed is:

1. A light-emitting device comprising:
a first electrode;
a first light-emitting layer over the first electrode;
a partition layer over the first light-emitting layer;
a second light-emitting layer over the partition layer; and
a second electrode over the second light-emitting layer;
wherein the second light-emitting layer includes an organometallic complex including a structure represented by a general formula (1),

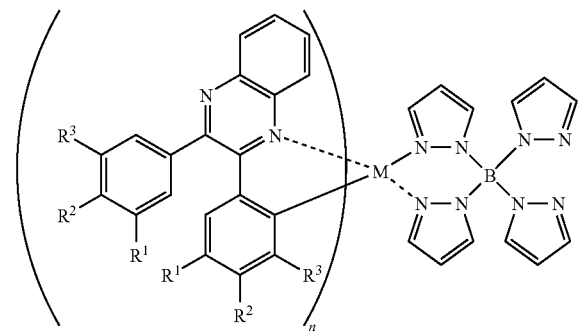

(1)

wherein each of R1 to R3 represents any one of hydrogen, a halogen group, an acyl group, an alkyl group, an alkoxyl group, an aryl group, a cyano group, and a heterocyclic group, at least one of $R^1$ to $R^3$ represents an electron-withdrawing group; and M represents a Group 9 element or a Group 10 element, and when M is the Group 9 element, n=2, whereas when M is the Group 10 element, n=1.

2. The light-emitting device according to claim 1, further comprising:
an electron injecting layer;
an electron transporting layer over the electron injecting layer;
a hole transporting layer; and
a hole injecting layer over the hole transporting layer,
wherein the electron injecting layer and the electron transporting layer are interposed between the first electrode and the first light-emitting layer,
wherein the hole transporting layer and the hole injecting layer are interposed between the second light-emitting layer and the second electrode.

3. The light-emitting device according to claim 1, wherein the electron-withdrawing group is any one of a halogen group, a haloalkyl group, and a cyano group.

4. The light-emitting device according to claim 1, wherein the electron-withdrawing group is either a fluoro group or a trifluoromethyl group.

5. The light-emitting device according to claim 1, wherein M is iridium or platinum.

6. The light-emitting device according to claim 1, wherein a CIE chromaticity coordinates is X≦0.69 and Y≧0.31.

7. A light-emitting device comprising:
a first electrode;
a first light-emitting layer over the first electrode;
a partition layer over the first light-emitting layer;
a second light-emitting layer over the partition layer; and
a second electrode over the second light-emitting layer;
wherein the second light-emitting layer includes an organometallic complex including a structure represented by a general formula (2), and

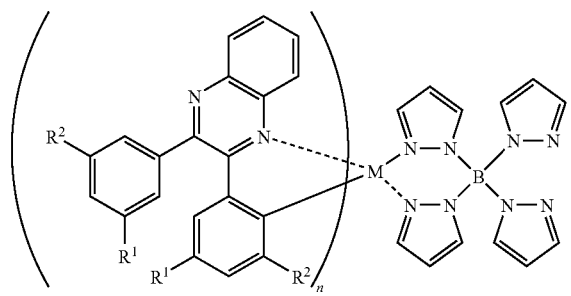

(2)

wherein each of $R^1$ and $R^2$ represents an electron-withdrawing group; and
M represents a Group 9 element or a Group 10 element, and when M is the Group 9 element, n=2, whereas when M is the Group 10 element, n=1.

8. The light-emitting device according to claim 7, further comprising:
an electron injecting layer;
an electron transporting layer over the electron injecting layer;
a hole transporting layer; and
a hole injecting layer over the hole transporting layer,
wherein the electron injecting layer and the electron transporting layer are interposed between the first electrode and the first light-emitting layer,
wherein the hole transporting layer and the hole injecting layer are interposed between the second light-emitting layer and the second electrode.

9. The light-emitting device according to claim 7, wherein the electron-withdrawing group is any one of a halogen group, a haloalkyl group, and a cyano group.

10. The light-emitting device according to claim 7, wherein the electron-withdrawing group is either a fluoro group or a trifluoromethyl group.

11. The light-emitting device according to claim 7, wherein M is iridium or platinum.

12. The light-emitting device according to claim 7, wherein a CIE chromaticity coordinates is X≦0.69 and Y≧0.31.

13. A light-emitting device comprising:
a first electrode;
a first light-emitting layer over the first electrode;
a partition layer over the first light-emitting layer;
a second light-emitting layer over the partition layer; and
a second electrode over the second light-emitting layer;
wherein the second light-emitting layer includes an organometallic complex including a structure represented by a general formula (3), and

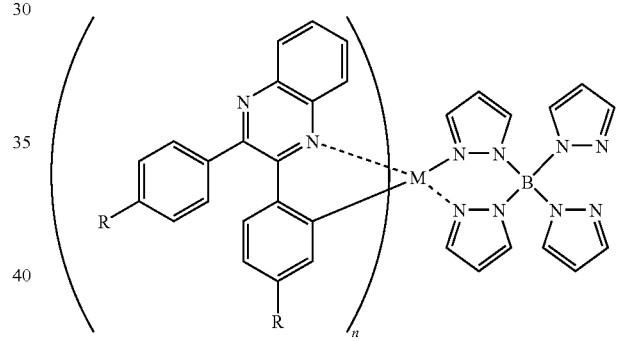

(3)

wherein R represents an electron-withdrawing group; and
M represents a Group 9 element or a Group 10 element, and when M is the Group 9 element, n=2, whereas when M is the Group 10 element, n=1.

14. The light-emitting device according to claim 13, further comprising:
an electron injecting layer;
an electron transporting layer over the electron injecting layer;
a hole transporting layer; and
a hole injecting layer over the hole transporting layer,
wherein the electron injecting layer and the electron transporting layer are interposed between the first electrode and the first light-emitting layer,
wherein the hole transporting layer and the hole injecting layer are interposed between the second light-emitting layer and the second electrode.

15. The light-emitting device according to claim 13, wherein the electron-withdrawing group is any one of a halogen group, a haloalkyl group, and a cyano group.

16. The light-emitting device according to claim 13, wherein the electron-withdrawing group is either a fluoro group or a trifluoromethyl group.

17. The light-emitting device according to claim 13, wherein M is iridium or platinum.

18. The light-emitting device according to claim 13, wherein a CIE chromaticity coordinates is X≦0.69 and Y≧0.31.

19. A light-emitting device comprising:
a cathode;
a first light-emitting layer over the cathode;
a hole transporting layer over the first light-emitting layer;
a first layer over the hole transporting layer;
a second layer over the first layer;
an electron transporting layer over the second layer;
a second light-emitting layer over the electron transporting layer; and
an anode over the second light-emitting layer;
wherein the second light-emitting layer includes an organometallic complex including a structure represented by a general formula (1),

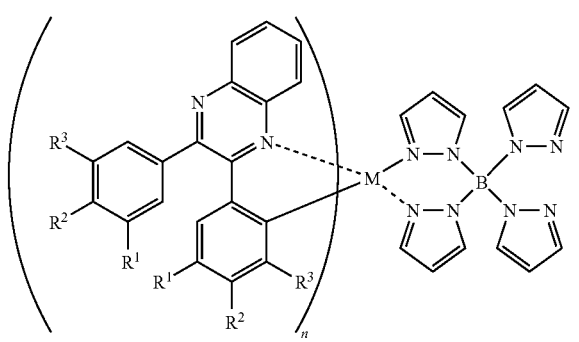

(1)

wherein each of R1 to R3 represents any one of hydrogen, a halogen group, an acyl group, an alkyl group, an alkoxyl group, an aryl group, a cyano group, and a heterocyclic group, at least one of $R^1$ to $R^3$ represents an electron-withdrawing group; and M represents a Group 9 element or a Group 10 element, and when M is the Group 9 element, n=2, whereas when M is the Group 10 element, n=1.

20. The light-emitting device according to claim 19,
wherein the first layer contains a first substance which has a higher transporting property of holes than that of electrons, and
wherein the second layer contains a second substance which has a higher transporting property of electrons than that of holes.

21. The light-emitting device according to claim 19, wherein the electron-withdrawing group is any one of a halogen group, a haloalkyl group, and a cyano group.

22. The light-emitting device according to claim 19, wherein the electron-withdrawing group is either a fluoro group or a trifluoromethyl group.

23. The light-emitting device according to claim 19, wherein M is iridium or platinum.

24. The light-emitting device according to claim 19, wherein a CIE chromaticity coordinates is X≦0.69 and Y≧0.31.

25. A light-emitting device comprising:
a cathode;
a first light-emitting layer over the cathode;
a hole transporting layer over the first light-emitting layer;
a first layer over the hole transporting layer;
a second layer over the first layer;
an electron transporting layer over the second layer;
a second light-emitting layer over the electron transporting layer; and
an anode over the second light-emitting layer;
wherein the second light-emitting layer includes an organometallic complex including a structure represented by a general formula (2), and

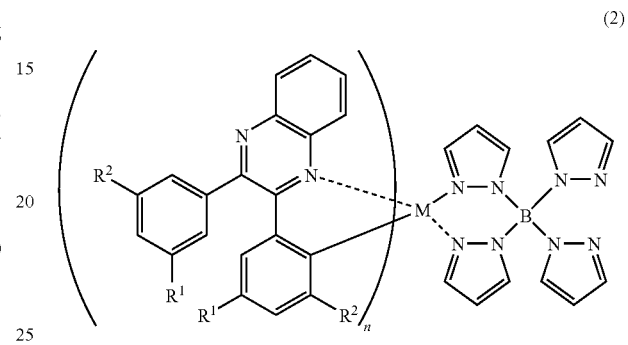

(2)

wherein each of $R^1$ and $R^2$ represents an electron-withdrawing group; and

M represents a Group 9 element or a Group 10 element, and when M is the Group 9 element, n=2, whereas when M is the Group 10 element, n=1.

26. The light-emitting device according to claim 25,
wherein the first layer contains a first substance which has a higher transporting property of holes than that of electrons, and
wherein the second layer contains a second substance which has a higher transporting property of electrons than that of holes.

27. The light-emitting device according to claim 25, wherein the electron-withdrawing group is any one of a halogen group, a haloalkyl group, and a cyano group.

28. The light-emitting device according to claim 25, wherein the electron-withdrawing group is either a fluoro group or a trifluoromethyl group.

29. The light-emitting device according to claim 25, wherein M is iridium or platinum.

30. The light-emitting device according to claim 25, wherein a CIE chromaticity coordinates is X≦0.69 and Y≧0.31.

31. A light-emitting device comprising:
a cathode;
a first light-emitting layer over the cathode;
a hole transporting layer over the first light-emitting layer;
a first layer over the hole transporting layer;
a second layer over the first layer;
an electron transporting layer over the second layer;
a second light-emitting layer over the electron transporting layer; and
an anode over the second light-emitting layer;
wherein the second light-emitting layer includes an organometallic complex including a structure represented by a general formula (3), and

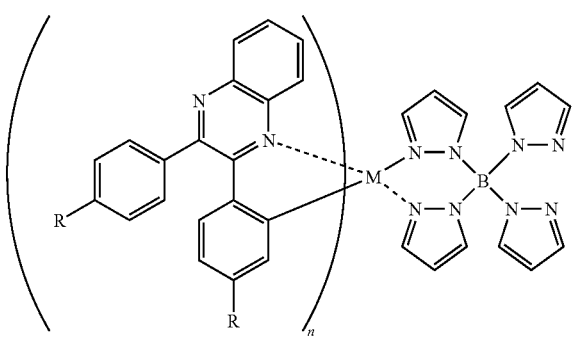

(3)

wherein R represents an electron-withdrawing group; and M represents a Group 9 element or a Group 10 element, and when M is the Group 9 element, n=2, whereas when M is the Group 10 element, n=1.

32. The light-emitting device according to claim 31, wherein the first layer contains a first substance which has a higher transporting property of holes than that of electrons, and
wherein the second layer contains a second substance which has a higher transporting property of electrons than that of holes.

33. The light-emitting device according to claim 31, wherein the electron-withdrawing group is any one of a halogen group, a haloalkyl group, and a cyano group.

34. The light-emitting device according to claim 31, wherein the electron-withdrawing group is either a fluoro group or a trifluoromethyl group.

35. The light-emitting device according to claim 31, wherein M is iridium or platinum.

36. The light-emitting device according to claim 31, wherein a CIE chromaticity coordinates is $X \leqq 0.69$ and $Y \geqq 0.31$.

* * * * *